(12) United States Patent
Dunkel et al.

(10) Patent No.: US 7,208,169 B2
(45) Date of Patent: Apr. 24, 2007

(54) BIPHENYL CARBOXAMIDES

(75) Inventors: Ralf Dunkel, Monheim (DE);
Hans-Ludwig Elbe, Wuppertal (DE);
Heiko Rieck, Ste. Foy-lès-Lyon (FR);
Robert Markert, Leverkusen (DE);
Ulrike Wachendorff-Neumann,
Neuwied (DE); Astrid Mauler-Machnik, Leichlingen (DE);
Karl-Heinz Kuck, Langenfeld (DE);
Martin Kugler, Leichlingen (DE);
Thomas Jaetsch, Köln (DE)

(73) Assignee: Bayer CropScience LP, Monheim (DE)

( * ) Notice: Subject to any disclaimer, the term of this patent is extended or adjusted under 35 U.S.C. 154(b) by 29 days.

(21) Appl. No.: 10/512,706

(22) PCT Filed: Apr. 16, 2003

(86) PCT No.: PCT/EP03/03964

§ 371 (c)(1),
(2), (4) Date: May 13, 2005

(87) PCT Pub. No.: WO03/093223

PCT Pub. Date: Nov. 13, 2003

(65) Prior Publication Data
US 2005/0272785 A1  Dec. 8, 2005

(30) Foreign Application Priority Data
Apr. 29, 2002  (DE) ................. 102 19 035

(51) Int. Cl.
*A01N 25/00* (2006.01)
*C07D 241/00* (2006.01)
*C07D 241/02* (2006.01)
*C07D 419/00* (2006.01)
*C07D 405/00* (2006.01)

(52) U.S. Cl. ............ 424/405; 544/336; 544/409; 544/410; 546/268.4; 546/281.7; 548/146; 548/206; 548/215; 548/269.7; 548/356.1; 548/364.1; 548/364.4; 549/13; 549/22; 549/60; 549/434; 549/435; 549/437; 549/439

(58) Field of Classification Search ............... 424/405; 544/336, 409, 410; 546/268.4, 281.7; 549/13, 549/22, 60, 434, 435, 437, 439; 548/146, 548/206, 215, 269.7, 356.1, 364.1, 364.4
See application file for complete search history.

(56) References Cited

U.S. PATENT DOCUMENTS

| | | | |
|---|---|---|---|
| 5,045,554 A | 9/1991 | Alt et al. | 514/365 |
| 5,223,526 A | 6/1993 | McLoughlin et al. | 514/406 |
| 5,330,995 A | 7/1994 | Eicken et al. | 514/355 |
| 5,416,103 A | 5/1995 | Eicken et al. | 514/355 |
| 5,438,070 A | 8/1995 | Eicken et al. | 514/403 |
| 5,480,897 A | 1/1996 | Eicken et al. | 514/365 |
| 5,556,988 A | 9/1996 | Eicken et al. | 548/374.1 |
| 5,589,493 A | 12/1996 | Eicken et al. | 514/355 |
| 5,633,218 A * | 5/1997 | Spedding et al. | 504/228 |
| 5,922,732 A | 7/1999 | Urch et al. | 514/304 |
| 5,968,947 A | 10/1999 | Urch et al. | 514/299 |
| 6,093,726 A | 7/2000 | Urch et al. | 514/299 |
| 6,147,104 A | 11/2000 | Eicken et al. | 514/406 |
| 6,174,894 B1 | 1/2001 | Urch et al. | 514/299 |
| 6,177,442 B1 | 1/2001 | Urch et al. | 514/299 |
| 6,207,676 B1 | 3/2001 | Urch et al. | 514/304 |
| 6,291,474 B1 | 9/2001 | Brightwell et al. | 514/299 |
| 6,369,093 B1 | 4/2002 | Elbe et al. | 514/406 |
| 6,391,882 B1 | 5/2002 | Moltzen et al. | 514/254.04 |
| 6,573,275 B1 | 6/2003 | Urch et al. | 514/304 |
| 2002/0061913 A1 | 5/2002 | Urch et al. | 514/366 |
| 2004/0082572 A1 | 4/2004 | Pineiro et al. | 514/220 |

FOREIGN PATENT DOCUMENTS

WO  91/01311  2/1991

OTHER PUBLICATIONS

Synth. Commun., 30, (month unavailable) 2000, pp. 665-669, Pravin M. Bendale et al, "Silica Gel Supported Chromium Trioxide: An Efficient Reagent For Oxidative Cleavage Of Oximes To Carbonyl Compounds Under Mild Condition".
Synth. Commun., 29 (month unavailable) 1999, pp. 1697-1701, A.R. Hajipour et al, "Solid-Phase Synthesis of Oximes".

* cited by examiner

*Primary Examiner*—Alton Pryor
(74) *Attorney, Agent, or Firm*—Richard E.L. Henderson

(57) ABSTRACT

The invention relates to novel biphenylcarboxamides of the formula (I)

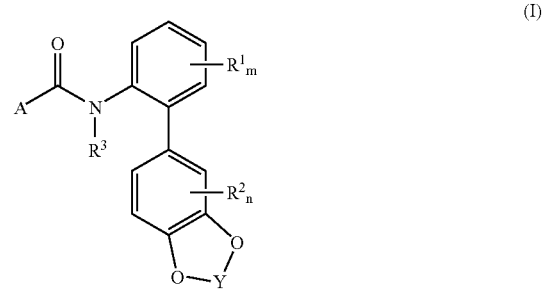

(I)

in which $R^1$, $R^2$, m, n, $R^3$, Y and A are as defined in the disclosure, to a plurality of processes for preparing these substances and their use for controlling unwanted microorganisms, and to novel intermediates and their preparation.

9 Claims, No Drawings

BIPHENYL CARBOXAMIDES

The present patent application has been filed under 35 U.S.C. 371 as a national stage application of PCT/EP03/03964, filed Apr. 16, 2003, which was published in German as International Patent Publication WO 03/003223 on Nov. 13, 2003, which is entitled to the right of priority of German Patent Application 102 19 035.6, filed Apr. 29, 2002.

The present invention relates to novel biphenylcarboxamides, to a plurality of processes for their preparation and to their use for controlling unwanted microorganisms.

It is already known that numerous carboxanilides have fungicidal properties (compare WO 93/11 117, WO 99/09 013, WO 00/14 071, EP-A 0 545 099 and EP-A 0 589 301). The activity of these substances is good; however, in some cases, for example at low application rates, it is unsatisfactory.

This invention now provides novel biphenylcarboxamides of the formula (I)

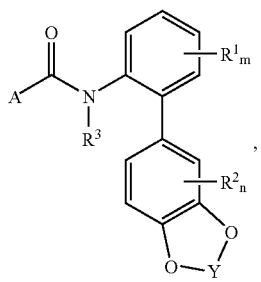

in which $R^1$ and $R^2$ independently of one another represent hydrogen, halogen, cyano, nitro, $C_1$–$C_8$-alkyl, $C_1$–$C_8$-alkoxy, $C_1$–$C_8$-alkylthio, $C_1$–$C_6$-haloalkyl, $C_1$–$C_6$-haloalkoxy or $C_1$–$C_6$-haloalkylthio having in each case 1 to 13 fluorine, chlorine and/or bromine atoms, m represents 1, 2, 3 or 4, where $R^1$ represents identical or different radicals if m represents 2, 3 or 4, n represents 1, 2 or 3, where $R^2$ represents identical or different radicals if n represents 2 or 3, $R^3$ represents hydrogen, hydroxyl, $C_1$–$C_6$-alkyl, $C_3$–$C_6$-cycloalkyl, $C_1$–$C_6$-alkoxy, $C_1$–$C_6$-alkoxy-$C_1$–$C_6$-alkyl, cyano-$C_1$–$C_6$-alkyl, $C_1$–$C_6$-haloalkyl having 1 to 7 halogen atoms, $C_1$–$C_6$-alkylamino, $C_1$–$C_6$-alkylsulphenyl, $C_1$–$C_6$-haloalkylsulphenyl having 1 to 7 halogen atoms, ($C_1$–$C_6$-alkyl)carbonyl, carbamoyl, Y represents carbonyl or represents $C_1$–$C_3$-alkylene which is optionally mono- or polysubstituted by identical or different substituents from the group consisting of halogen, $C_1$–$C_6$-alkyl, $C_1$–$C_6$-alkoxy, $C_1$–$C_6$-alkylthio, $C_1$–$C_6$-haloalkyl, $C_1$–$C_6$-haloalkoxy and/or $C_1$–$C_6$-haloalkylthio having in each case 1 to 13 fluorine, chlorine and/or bromine atoms and A represents a radical of the formula

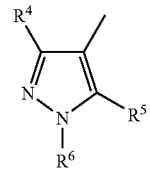

where $R^4$ represents hydrogen, cyano, halogen, nitro, $C_1$–$C_4$-alkyl, $C_1$–$C_4$-haloalkyl having 1 to 5 halogen atoms, $C_3$–$C_6$-cycloalkyl, $C_1$–$C_4$-alkoxy, $C_1$–$C_4$-haloalkoxy having 1 to 5 halogen atoms, $C_1$–$C_4$-alkylthio, $C_1$–$C_4$-haloalkylthio having 1 to 5 halogen atoms, aminocarbonyl or aminocarbonyl-$C_1$–$C_4$-alkyl and $R^5$ represents hydrogen, halogen, cyano, $C_1$–$C_4$-alkyl, $C_1$–$C_4$-alkoxy or $C_1$–$C_4$-alkylthio and $R^6$ represents hydrogen, $C_1$–$C_4$-alkyl, $C_1$–$C_4$-haloalkyl having 1 to 5 halogen atoms, hydroxy-$C_1$–$C_4$-alkyl, $C_2$–$C_6$-alkenyl, $C_3$–$C_6$-cycloalkyl, $C_1$–$C_4$-alkylthio-$C_1$–$C_4$-alkyl, $C_1$–$C_4$-haloalkylthio-$C_1$–$C_4$-alkyl having 1 to 5 halogen atoms, $C_1$–$C_4$-alkoxy-$C_1$–$C_4$-alkyl, $C_1$–$C_4$-haloalkoxy-$C_1$–$C_4$-alkyl having 1 to 5 halogen atoms or phenyl, or A represents a radical of the formula

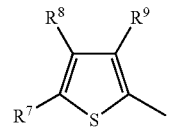

where $R^7$ and $R^8$ independently of one another represent hydrogen, halogen, $C_1$–$C_4$-alkyl or $C_1$–$C_4$-haloalkyl having 1 to 5 halogen atoms and $R^9$ represents halogen, cyano or $C_1$–$C_4$-alkyl or $C_1$–$C_4$-haloalkoxy having 1 to 5 halogen atoms, or A represents a radical of the formula

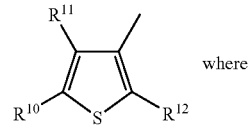

where $R^{10}$ and $R^{11}$ independently of one another represent hydrogen, halogen, $C_1$–$C_4$-alkyl or $C_1$–$C_4$-haloalkyl having 1 to 5 halogen atoms and $R^{12}$ represents hydrogen, $C_1$–$C_4$-alkyl or halogen, or A represents a radical of the formula

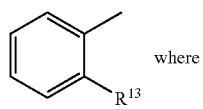 where

R¹³ represents hydrogen, halogen, hydroxyl, cyano, $C_1$–$C_6$-alkyl, $C_1$–$C_4$-haloalkyl having 1 to 5 halogen atoms, $C_1$–$C_4$-haloalkoxy having 1 to 5 halogen atoms or $C_1$–$C_4$-haloalkylthio having 1 to 5 halogen atoms, or
A represents a radical of the formula

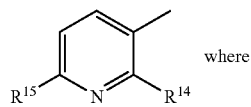 where

R¹⁴ represents halogen, hydroxyl, cyano, $C_1$–$C_4$-alkyl, $C_1$–$C_4$-haloalkyl having 1 to 5 halogen atoms, $C_1$–$C_4$-alkoxy, $C_1$–$C_4$-alkylthio, $C_1$–$C_4$-haloalkylthio having 1 to 5 halogen atoms, or $C_1$–$C_4$-haloalkoxy having 1 to 5 halogen atoms and R¹⁵ represents hydrogen, halogen, cyano, $C_1$–$C_4$-alkyl, $C_1$–$C_4$-haloalkyl having 1 to 5 halogen atoms, $C_1$–$C_4$-alkoxy, $C_1$–$C_4$-alkylthio, $C_1$–$C_4$-haloalkoxy having 1 to 5 halogen atoms, $C_1$–$C_4$-alkylsulphinyl or $C_1$–$C_4$-alkylsulphonyl, or
A represents a radical of the formula

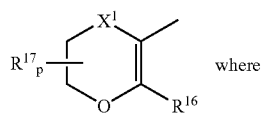 where

R¹⁶ represents $C_1$–$C_4$-alkyl or $C_1$–$C_4$-haloalkyl having 1 to 5 halogen atoms and R¹⁷ represents $C_1$–$C_4$-alkyl, X¹ represents a sulphur atom, represents SO, SO₂ or CH₂, p represents 0, 1 or 2, where R¹⁷ represents identical or different radicals if p represents 2, or
A represents a radical of the formula

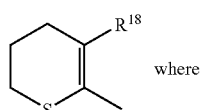 where

R¹⁸ represents $C_1$–$C_4$-alkyl or $C_1$–$C_4$-haloalkyl having 1 to 5 halogen atoms, or A represents a radical of the formula

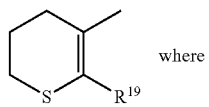 where

R¹⁹ represents $C_1$–$C_4$-alkyl or $C_1$–$C_4$-haloalkyl having 1 to 5 halogen atoms, or
A represents a radical of the formula

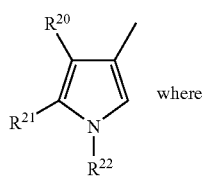 where

R²⁰ represents halogen, cyano, $C_1$–$C_4$-alkyl or $C_1$–$C_4$-haloalkyl having 1 to 5 halogen atoms, R²¹ represents hydrogen, halogen, $C_1$–$C_4$-alkyl or $C_1$–$C_4$-haloalkyl having 1 to 5 halogen atoms and R²² represents hydrogen, cyano, $C_1$–$C_4$-alkyl, $C_1$–$C_4$-haloalkyl having 1 to 5 halogen atoms, $C_1$–$C_4$-alkoxy-$C_1$–$C_4$-alkyl, hydroxy-$C_1$–$C_4$-alkyl, $C_1$–$C_4$-alkylsulphonyl, di($C_1$–$C_4$-alkyl)aminosulphonyl, $C_1$–$C_6$-alkylcarbonyl or optionally substituted phenylsulphonyl or benzoyl, or
A represents a radical of the formula

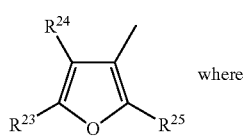 where

R²³ and R²⁴ independently of one another represent hydrogen, halogen, amino, $C_1$–$C_4$-alkyl or $C_1$–$C_4$-haloalkyl having 1 to 5 halogen atoms and R²⁵ represents hydrogen, halogen, $C_1$–$C_4$-alkyl or $C_1$–$C_4$-haloalkyl having 1 to 5 halogen atoms, or
A represents a radical of the formula

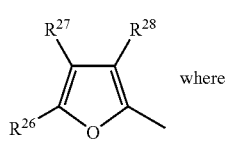 where

R²⁶ and R²⁷ independently of one another represent hydrogen, halogen, amino, nitro, $C_1$–$C_4$-alkyl or $C_1$–$C_4$-haloalkyl having 1 to 5 halogen atoms and R²⁸ represents hydrogen, halogen, $C_1$–$C_4$-alkyl or $C_1$–$C_4$-haloalkyl having 1 to 5 halogen atoms, or A represents a radical of the formula

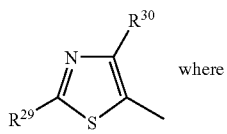 where

R²⁹ represents hydrogen, halogen, amino, $C_1$–$C_4$-alkylamino, di-($C_1$–$C_4$-alkyl)amino, cyano, $C_1$–$C_4$-alkyl or $C_1$–$C_4$-haloalkyl having 1 to 5 halogen atoms and
R³⁰ represents halogen, $C_1$–$C_4$-alkyl or $C_1$–$C_4$-haloalkyl having 1 to 5 halogen atoms, or A represents a radical of the formula

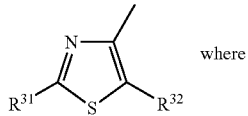 where

R³¹ represents hydrogen, halogen, amino, $C_1$–$C_4$-alkylamino, di-($C_1$–$C_4$-alkyl)amino, cyano, $C_1$–$C_4$-alkyl or $C_1$–$C_4$-haloalkyl having 1 to 5 halogen atoms and
R³² represents halogen, $C_1$–$C_4$-alkyl or $C_1$–$C_4$-haloalkyl having 1 to 5 halogen atoms, or A represents a radical of the formula

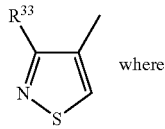 where

R³³ represents halogen, $C_1$–$C_4$-alkyl or $C_1$–$C_4$-haloalkyl having 1 to 5 halogen atoms, or A represents a radical of the formula

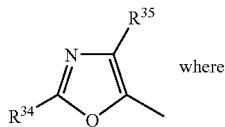 where

R³⁴ represents hydrogen or $C_1$–$C_4$-alkyl and
R³⁵ represents halogen or $C_1$–$C_4$-alkyl, or A represents a radical of the formula

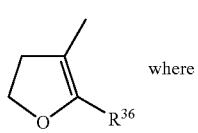 where

R³⁶ represents $C_1$–$C_4$-alkyl or $C_1$–$C_4$-haloalkyl having 1 to 5 halogen atoms, or A represents a radical of the formula

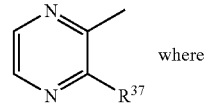 where

R³⁷ represents hydrogen, halogen or $C_1$–$C_4$-alkyl.

Depending on the nature of the substituents, the compounds of the formula (I) can be present as geometrical and/or optical isomers or isomer mixtures of varying compositions. The invention relates both to the use of the pure isomers and to that of the isomer mixture.

Furthermore, it has been found that biphenylcarboxamides of the formula (I) are obtained when
a) carboxylic acid derivatives of the formula (II)

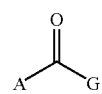 (II)

in which
A is as defined above and
G represents halogen, hydroxyl or $C_1$–$C_6$-alkoxy,
are reacted with aniline derivatives of the formula (III)

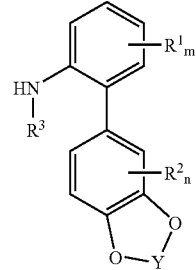 (III)

in which
R¹, R², m, n, R³ and Y are as defined above,
if appropriate in the presence of a catalyst, if appropriate in the presence of an acid binder and if appropriate in the presence of a diluent, or b) carboxamide derivatives of the formula (IV)

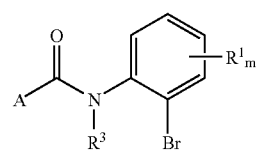 (IV)

in which $R^1$, m, $R^3$ and A are as defined above, are reacted with boronic acid derivatives of the formula (V)

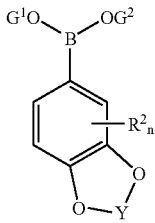

(V)

in which $R^2$, n and Y are as defined above and $G^1$ and $G^2$ each represent hydrogen or together represent tetramethylethylene, in the presence of a catalyst, if appropriate in the presence of an acid binder and if appropriate in the presence of a diluent, or c) carboxamide boronic acid derivatives of the formula (VI)

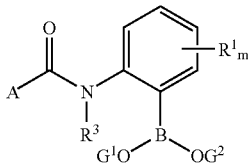

(VI)

in which $R^1$, m, $R^3$ and A are as defined above and $G^1$ and $G^2$ each represent hydrogen or together represent tetramethylethylene, are reacted with phenyl derivatives of the formula (VII)

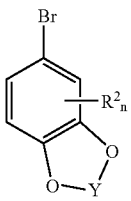

(VII)

in which $R^2$, n and Y are as defined above, in the presence of a catalyst, if appropriate in the presence of an acid binder and if appropriate in the presence of a diluent, or d) carboxamide derivatives of the formula (IV)

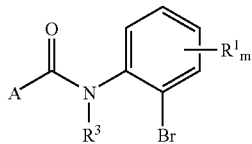

(IV)

in which $R^1$, m, $R^3$ and A are as defined above, are reacted with phenyl derivatives of the formula (VII)

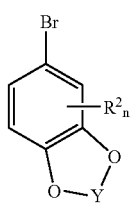

(VII)

in which $R^2$, n and Y are as defined above, in the presence of a palladium or platinum catalyst and in the presence of 4,4,4',4',5,5,5',5'-octamethyl-2,2'-bis-1,3,2-dioxaborolane, if appropriate in the presence of an acid binder and if appropriate in the presence of a diluent.

Finally, it has been found that the novel biphenylcarboxamides of the formula (I) have very good microbicidal properties and can be used for controlling unwanted microorganisms both in crop protection and in the protection of materials.

Surprisingly, the biphenylcarboxamides of the formula (I) according to the invention have considerably better fungicidal activity than the constitutionally most similar active compounds of the prior art having the same direction of action.

The formula (I) provides a general definition of the biphenylcarboxamides according to the invention.

Preference is given to biphenylcarboxamides of the formula (I) in which $R^1$ and $R^2$ independently of one another represent hydrogen, fluorine, chlorine, bromine, cyano, nitro, $C_1$–$C_6$-alkyl, $C_1$–$C_6$-alkoxy, $C_1$–$C_6$-alkylthio, $C_1$–$C_4$-haloalkyl, $C_1$–$C_4$-haloalkoxy, $C_1$–$C_4$-haloalkylthio having in each case 1 to 9 fluorine, chlorine and/or bromine atoms, m represents 1, 2 or 3, where $R^1$ represents identical or different radicals if m represents 2 or 3, n represents 1, 2 or 3, where $R^2$ represents identical or different radicals if n represents 2 or 3, $R^3$ represents hydrogen, hydroxyl, $C_1$–$C_4$-alkyl, $C_3$–$C_6$-cycloalkyl, $C_1$–$C_4$-alkoxy, $C_1$–$C_3$-alkoxy-$C_1$–$C_2$-alkyl, cyano-$C_1$–$C_4$-alkyl, $C_1$–$C_4$-haloalkyl having 1 to 5 halogen atoms, $C_1$–$C_4$-aminoalkyl, $C_1$–$C_4$-alkylsulphenyl, $C_1$–$C_4$-haloalkylsulphenyl having 1 to 5 halogen atoms, ($C_1$–$C_4$-alkyl)carbonyl, Y represents carbonyl or represents $C_1$–$C_2$-alkylene which is optionally mono- or polysubstituted by identical or different substituents from the group consisting of fluorine, chlorine, bromine, $C_1$–$C_4$-alkyl, $C_1$–$C_4$-alkoxy, $C_1$–$C_4$-alkylthio, $C_1$–$C_4$-haloalkyl, $C_1$–$C_4$-haloalkoxy and/or $C_1$–$C_4$-haloalkylthio having in each case 1 to 9 fluorine, chlorine and/or bromine atoms, and
A represents a radical of the formula

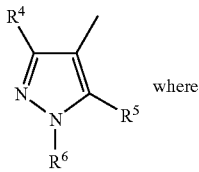 where

R$^4$ represents hydrogen, cyano, fluorine, chlorine, bromine, iodine, methyl, ethyl, i-propyl, $C_1$–$C_2$-haloalkyl having 1 to 5 fluorine, chlorine and/or bromine atoms, cyclopropyl, methoxy, ethoxy, $C_1$–$C_2$-haloalkoxy having 1 to 5 fluorine, chlorine and/or bromine atoms, methylthio, ethylthio, trifluoromethylthio, difluoromethylthio, aminocarbonyl, aminocarbonylmethyl or aminocarbonylethyl, R$^5$ represents hydrogen, fluorine, chlorine, bromine, iodine, methyl, ethyl, methoxy, ethoxy, methylthio or ethylthio and R$^6$ represents hydrogen, methyl, ethyl, n-propyl, i-propyl, $C_1$–$C_2$-haloalkyl having 1 to 5 fluorine, chlorine and/or bromine atoms, hydroxymethyl, hydroxyethyl, cyclopropyl, cyclopentyl, cyclohexyl or phenyl, or
A represents a radical of the formula

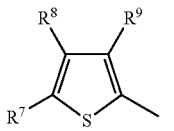 where

R$^7$ and R$^8$ independently of one another represent hydrogen, fluorine, chlorine, bromine, methyl, ethyl or $C_1$–$C_2$-haloalkyl having 1 to 5 fluorine, chlorine and/or bromine atoms and R$^9$ represents fluorine, chlorine, bromine, cyano, methyl, ethyl or $C_1$–$C_2$-haloalkoxy having 1 to 5 fluorine, chlorine and/or bromine atoms, or
A represents a radical of the formula

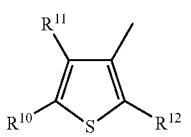 where

R$^{10}$ and R$^{11}$ independently of one another represent hydrogen, fluorine, chlorine, bromine, methyl, ethyl or $C_1$–$C_2$-haloalkyl having 1 to 5 fluorine, chlorine and/or bromine atoms and R$^{12}$ represents hydrogen, fluorine, chlorine, bromine, methyl or ethyl, or A represents a radical of the formula

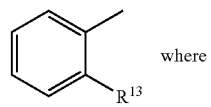 where

R$^{13}$ represents hydrogen, fluorine, chlorine, bromine, iodine, hydroxyl, cyano, $C_1$–$C_4$-alkyl, $C_1$–$C_2$-haloalkyl having 1 to 5 fluorine, chlorine and/or bromine atoms, $C_1$–$C_2$-haloalkoxy having 1 to 5 fluorine, chlorine and/or bromine atoms or $C_1$–$C_2$-haloalkylthio having 1 to 5 fluorine, chlorine and/or bromine atoms, or
A represents a radical of the formula

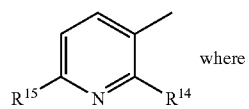 where

R$^{14}$ represents fluorine, chlorine, bromine, iodine, hydroxyl, cyano, $C_1$–$C_4$-alkyl, $C_1$–$C_2$-haloalkyl having 1 to 5 fluorine, chlorine and/or bromine atoms, methoxy, ethoxy, methylthio, ethylthio, difluoromethylthio, trifluoromethylthio or $C_1$–$C_2$-haloalkoxy having 1 to 5 fluorine, chlorine and/or bromine atoms and R$^{15}$ represents hydrogen, fluorine, chlorine, bromine, iodine, cyano, $C_1$–$C_4$-alkyl, $C_1$–$C_2$-haloalkyl having 1 to 5 fluorine, chlorine and/or bromine atoms, methoxy, ethoxy, methylthio, ethylthio, $C_1$–$C_2$-haloalkoxy having 1 to 5 fluorine, chlorine and/or bromine atoms, $C_1$–$C_2$-alkylsulphinyl or $C_1$–$C_2$-alkylsulphonyl, or
A represents a radical of the formula

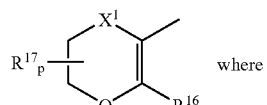 where

R$^{16}$ represents methyl, ethyl or $C_1$–$C_2$-haloalkyl having 1 to 5 fluorine, chlorine and/or bromine atoms and R$^{17}$ represents methyl or ethyl, X$^1$ represents a sulphur atom, represents SO, SO$_2$ or CH$_2$ and p represents 0, 1 or 2, where R$^{17}$ represents identical or different radicals if p represents 2, or
A represents a radical of the formula

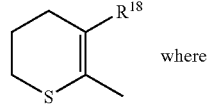 where

R$^{18}$ represents methyl, ethyl or $C_1$–$C_2$-haloalkyl having 1 to 5 fluorine, chlorine and/or bromine atoms, or A represents a radical of the formula

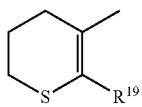 where $R^{19}$ represents methyl, ethyl or $C_1$–$C_2$-haloalkyl having 1 to 5 fluorine, chlorine and/or bromine atoms, or
A represents a radical of the formula

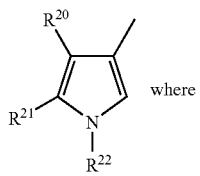 where $R^{20}$ represents fluorine, chlorine, bromine, cyano, methyl, ethyl, i-propyl or $C_1$–$C_2$-haloalkyl having 1 to 5 fluorine, chlorine and/or bromine atoms, $R^{21}$ represents hydrogen, fluorine, chlorine, bromine, methyl, ethyl or $C_1$–$C_2$-haloalkyl having 1 to 5 fluorine, chlorine and/or bromine atoms and $R^{22}$ represents hydrogen, methyl, ethyl, $C_1$–$C_2$-haloalkyl having 1 to 5 fluorine, chlorine and/or bromine atoms, $C_1$–$C_2$-alkoxy-$C_1$–$C_2$-alkyl, hydroxymethyl, hydroxyethyl, methylsulphonyl or dimethylaminosulphonyl, or
A represents a radical of the formula

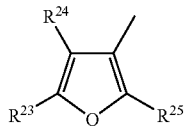 where $R^{23}$ and $R^{24}$ independently of one another represent hydrogen, fluorine, chlorine, bromine, amino, methyl, ethyl or $C_1$–$C_2$-haloalkyl having 1 to 5 fluorine, chlorine and/or bromine atoms and $R^{25}$ represents hydrogen, fluorine, chlorine, bromine, methyl, ethyl or $C_1$–$C_2$-haloalkyl having 1 to 5 fluorine, chlorine and/or bromine atoms, or
A represents a radical of the formula

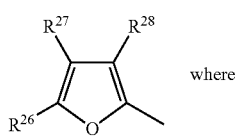 where $R^{26}$ and $R^{27}$ independently of one another represent hydrogen, fluorine, chlorine, bromine, amino, nitro, methyl, ethyl or $C_1$–$C_2$-haloalkyl having 1 to 5 fluorine, chlorine and/or bromine atoms and $R^{28}$ represents hydrogen, fluorine, chlorine, bromine, methyl, ethyl or $C_1$–$C_2$-haloalkyl having 1 to 5 fluorine, chlorine and/or bromine atoms, or
A represents a radical of the formula

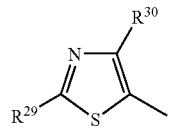 where $R^{29}$ represents hydrogen, fluorine, chlorine, bromine, amino, $C_1$–$C_4$-alkylamino, di($C_1$–$C_4$-alkyl)amino, cyano, methyl, ethyl or $C_1$–$C_2$-haloalkyl having 1 to 5 fluorine, chlorine and/or bromine atoms and $R^{30}$ represents fluorine, chlorine, bromine, methyl, ethyl or $C_1$–$C_2$-haloalkyl having 1 to 5 fluorine, chlorine and/or bromine atoms, or
A represents a radical of the formula

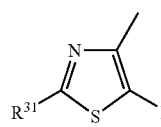 where $R^{31}$ represents hydrogen, fluorine, chlorine, bromine, amino, $C_1$–$C_4$-alkylamino, di($C_1$–$C_4$-alkyl)amino, cyano, methyl, ethyl or $C_1$–$C_2$-haloalkyl having 1 to 5 fluorine, chlorine and/or bromine atoms and $R^{32}$ represents fluorine, chlorine, bromine, methyl, ethyl or $C_1$–$C_2$-haloalkyl having 1 to 5 fluorine, chlorine and/or bromine atoms, or
A represents a radical of the formula

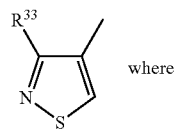 where $R^{33}$ represents fluorine, chlorine, bromine, methyl, ethyl or $C_1$–$C_2$-haloalkyl having 1 to 5 fluorine, chlorine and/or bromine atoms, or
A represents a radical of the formula

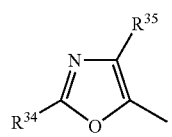 where $R^{34}$ represents hydrogen, methyl or ethyl and
$R^{35}$ represents fluorine, chlorine, bromine, methyl or ethyl, or A represents a radical of the formula

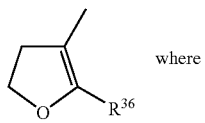
where $R^{36}$ represents methyl, ethyl or $C_1$–$C_2$-haloalkyl having 1 to 5 fluorine, chlorine and/or bromine atoms, or A represents a radical of the formula

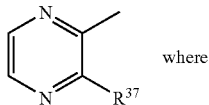
where $R^{37}$ represents hydrogen, fluorine, chlorine, bromine, methyl or ethyl.

Particular preference is given to biphenylcarboxamides of the formula (I) in which $R^1$ and $R^2$ independently of one another represent hydrogen, fluorine, chlorine, bromine, cyano, nitro, methyl, ethyl, n-propyl, i-propyl, n-butyl, i-butyl, s-butyl, t-butyl, methoxy, ethoxy, methylthio, ethylthio, trichloromethyl, trifluoromethyl, difluoromethyl, difluorochloromethyl, difluoromethoxy, trifluoromethoxy, trifluoromethylthio, difluorochloromethylthio, m represents 1 or 2, where $R^1$ represents identical or different radicals if m represents 2, n represents 1 or 2, where $R^2$ represents identical or different radicals if n represents 2, $R^3$ represents hydrogen, hydroxyl, methyl, ethyl, n-propyl, i-propyl, n-, i-, s-, t-butyl, cyclopropyl, cyclobutyl, cyclopentyl, cyclohexyl, methoxy, ethoxy, methoxymethyl, cyanomethyl, difluoromethyl, methylsulphenyl, trichloromethylsulphenyl or acetyl, Y represents carbonyl or represents —$CH_2$— or —$(CH_2)_2$—, each of which is optionally mono- to tetra-substituted by identical or different substituents from the group consisting of fluorine, chlorine, bromine, methyl, ethyl, i-propyl, t-butyl, methoxy, i-propoxy, t-butoxy, methylthio, i-propylthio, t-butylthio, trifluoromethyl, trifluoromethoxy and trifluoromethylthio, and A represents a radical of the formula

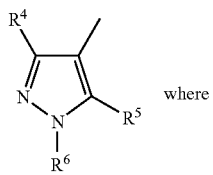
where $R^4$ represents hydrogen, fluorine, chlorine, bromine, iodine, methyl, ethyl, i-propyl, monofluoromethyl, difluoromethyl, trifluoromethyl, difluorochloromethyl, trichloromethyl, cyclopropyl, methoxy, ethoxy, trifluoromethoxy, trichloromethoxy, methylthio, ethylthio, trifluoromethylthio or difluoromethylthio and $R^5$ represents hydrogen, fluorine, chlorine, bromine, iodine, methyl, ethyl, methoxy, ethoxy, methylthio or ethylthio and $R^6$ represents hydrogen, methyl, ethyl, trifluoromethyl, difluoromethyl, hydroxymethyl, hydroxyethyl or phenyl, or A represents a radical of the formula

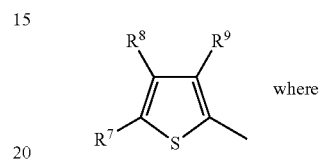
where $R^7$ and $R^8$ independently of one another represent hydrogen, fluorine, chlorine, bromine, methyl, ethyl, difluoromethyl, trifluoromethyl, difluorochloromethyl or trichloromethyl and $R^9$ represents fluorine, chlorine, bromine, cyano, methyl, trifluoromethoxy, difluoromethoxy, difluorochloromethoxy or trichloromethoxy, or A represents a radical of the formula

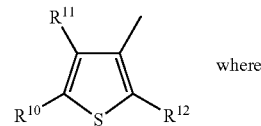
where $R^{10}$ and $R^{11}$ independently of one another represent hydrogen, fluorine, chlorine, bromine, methyl, ethyl, difluoromethyl, trifluoromethyl, difluorochloromethyl or trichloromethyl and $R^{12}$ represents hydrogen, fluorine, chlorine, bromine, methyl or ethyl, or A represents a radical of the formula

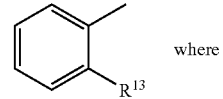
where $R^{13}$ represents hydrogen, fluorine, chlorine, bromine, iodine, hydroxyl, cyano, methyl, ethyl, n-propyl, i-propyl, n-butyl, i-butyl, s-butyl, t-butyl, difluoromethyl, trifluoromethyl, difluorochloromethyl, trichloromethyl, trifluoromethoxy, difluoromethoxy, difluorochloromethoxy, trichloromethoxy, trifluoromethylthio, difluoromethylthio, difluorochloromethylthio or trichloromethylthio, or A represents a radical of the formula

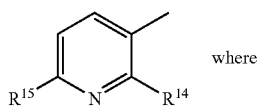 where

R[14] represents fluorine, chlorine, bromine, iodine, hydroxyl, cyano, methyl, ethyl, n-propyl, i-propyl, n-butyl, i-butyl, s-butyl, t-butyl, trifluoromethyl, difluoromethyl, difluorochloromethyl, trichloromethyl, methoxy, ethoxy, methylthio, ethylthio, difluoromethylthio, trifluoromethylthio, trifluoromethoxy, difluoromethoxy, difluorochloromethoxy or trichloromethoxy and R[15] represents hydrogen, fluorine, chlorine, bromine, iodine, cyano, n-propyl, i-propyl, n-butyl, i-butyl, s-butyl, t-butyl, trifluoromethyl, difluoromethyl, difluorochloromethyl, trichloromethyl, methoxy, ethoxy, methylthio, ethylthio, trifluoromethoxy, difluoromethoxy, difluorochloromethoxy, trichloromethoxy, methylsulphinyl or methylsulphonyl, or
A represents a radical of the formula

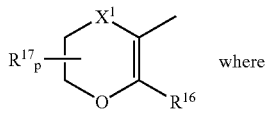 where

R[16] represents methyl, ethyl, trifluoromethyl, difluoromethyl, difluorochloromethyl or trichloromethyl and R[17] represents methyl or ethyl, X[1] represents a sulphur atom, represents SO, SO$_2$ or CH$_2$ and p represents 0, 1 or 2, where R[17] represents identical or different radicals if p represents 2, or
A represents a radical of the formula

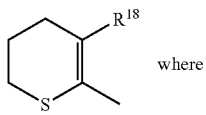 where

R[18] represents methyl, ethyl, trifluoromethyl, difluoromethyl, difluorochloromethyl or trichloromethyl, or
A represents a radical of the formula

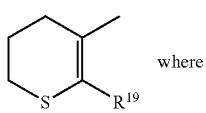 where

R[19] represents methyl, ethyl, trifluoromethyl, difluoromethyl, difluorochloromethyl or trichloromethyl, or A represents a radical of the formula

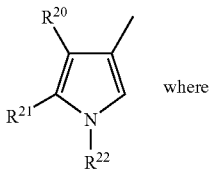 where

R[20] represents fluorine, chlorine, bromine, cyano, methyl, ethyl, i-propyl, trifluoromethyl, difluoromethyl, difluorochloromethyl or trichloromethyl, R[21] represents hydrogen, fluorine, chlorine, bromine, methyl, ethyl, trifluoromethyl, difluoromethyl or trichloromethyl and R[22] represents hydrogen, methyl, ethyl, trifluoromethyl, methoxymethyl, ethoxymethyl, hydroxymethyl or hydroxyethyl, or
A represents a radical of the formula

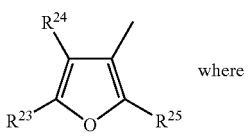 where

R[23] and R[24] independently of one another represent hydrogen, fluorine, chlorine, bromine, methyl, ethyl, trifluoromethyl, difluoromethyl, difluorochloromethyl or trichloromethyl and R[25] represents hydrogen, fluorine, chlorine, bromine, methyl, ethyl, trifluoromethyl, difluoromethyl, difluorochloromethyl or trichloromethyl, or
A represents a radical of the formula

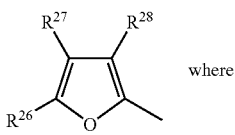 where

R[26] and R[27] independently of one another represent hydrogen, fluorine, chlorine, bromine, nitro, methyl, ethyl, trifluoromethyl, difluoromethyl, difluorochloromethyl or trichloromethyl and R[28] represents hydrogen, fluorine, chlorine, bromine, methyl, ethyl, trifluoromethyl, difluoromethyl, difluorochloromethyl or trichloromethyl, or
A represents a radical of the formula

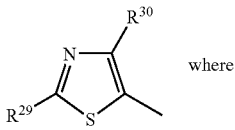 where

R[29] represents hydrogen, fluorine, chlorine, bromine, amino, methylamino, dimethylamino, cyano, methyl, ethyl, trifluoromethyl, difluoromethyl, difluorochloromethyl or trichloromethyl and R$^{30}$ represents fluorine, chlorine, bromine, methyl, ethyl, trifluoromethyl, difluoromethyl, difluorochloromethyl or trichloromethyl, or
A represents a radical of the formula

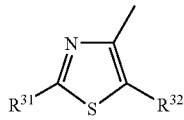

where

R$^{31}$ represents hydrogen, fluorine, chlorine, bromine, amino, methylamino, dimethylamino, cyano, methyl, ethyl, trifluoromethyl, difluoromethyl, difluorochloromethyl or trichloromethyl and R$^{32}$ represents fluorine, chlorine, bromine, methyl, ethyl, trifluoromethyl, difluoromethyl, difluorochloromethyl or trichloromethyl, or
A represents a radical of the formula

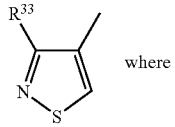

where

R$^{33}$ represents fluorine, chlorine, bromine, methyl, ethyl, trifluoromethyl, difluoromethyl, difluorochloromethyl or trichloromethyl, or
A represents a radical of the formula

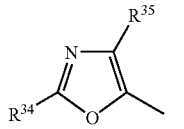

where

R$^{34}$ represents hydrogen, methyl or ethyl and

R$^{35}$ represents fluorine, chlorine, bromine, methyl or ethyl, or
A represents a radical of the formula

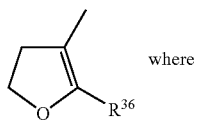

where

R$^{36}$ represents methyl, ethyl, trifluoromethyl, difluoromethyl, difluorochloromethyl or trichloromethyl, or A represents a radical of the formula

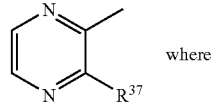

where

R$^{37}$ represents hydrogen, fluorine, chlorine, bromine, methyl or ethyl.

Very particular preference is given to biphenylcarboxamides of the formula (I) in which R$^1$ and R$^2$ independently of one another represent hydrogen, fluorine, chlorine, bromine, methyl, ethyl, n-propyl, i-propyl, n-butyl, i-butyl, s-butyl, t-butyl, methoxy, ethoxy, methylthio, ethylthio, trichloromethyl, trifluoromethyl, difluoromethyl, trifluoromethoxy, trifluoromethylthio, m represents 1 or 2, where R$^1$ represents identical or different radicals if m represents 2, n represents 1, R$^3$ represents hydrogen, methyl, ethyl, n-propyl, i-propyl, n-, i-, s-, t-butyl, cyclopropyl, cyclopentyl or cyclohexyl, Y represents carbonyl or represents —CH$_2$— or —(CH$_2$)$_2$—, each of which is optionally mono- to tetra-substituted by identical or different substituents from the group consisting of fluorine, methyl, i-propyl, t-butyl, methoxy, i-propoxy, t-butoxy, methylthio, i-propylthio, t-butylthio, trifluoromethyl, trifluoromethoxy and trifluoromethylthio, and
A represents a radical of the formula

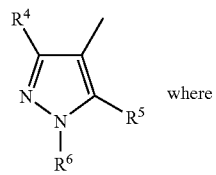

where

R$^4$ represents hydrogen, fluorine, chlorine, bromine, iodine, methyl, i-propyl, monofluoromethyl, difluoromethyl, trifluoromethyl, difluorochloromethyl or trichloromethyl and R$^5$ represents hydrogen, fluorine, chlorine, bromine, iodine or methyl and R$^6$ represents hydrogen, methyl, trifluoromethyl or phenyl, or
A represents a radical of the formula

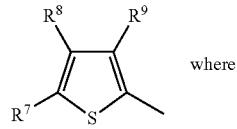

where

R$^7$ and R$^8$ independently of one another represent hydrogen, fluorine, chlorine, bromine, methyl, ethyl, difluoromethyl, trifluoromethyl or trichloromethyl and R$^9$ represents fluorine, chlorine, bromine, methyl or trifluoromethoxy, or A represents a radical of the formula

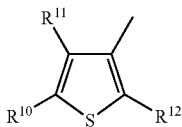 where

R$^{10}$ and R$^{11}$ independently of one another represent hydrogen, fluorine, chlorine, bromine, methyl, ethyl, difluoromethyl, trifluoromethyl or trichloromethyl and
R$^{12}$ represents hydrogen, fluorine, chlorine, bromine or methyl, or
A represents a radical of the formula

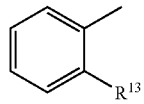 where

R$^{13}$ represents hydrogen, fluorine, chlorine, bromine, iodine, methyl, difluoromethyl, trifluoromethyl or trichloromethyl, or
A represents a radical of the formula

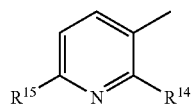 where

R$^{14}$ represents fluorine, chlorine, bromine, iodine, methyl, trifluoromethyl, difluoromethyl or trichloromethyl and
R$^{15}$ represents hydrogen, fluorine, chlorine, bromine, iodine, n-propyl, i-propyl, n-butyl, i-butyl, s-butyl, t-butyl, trifluoromethyl, difluoromethyl, trichloromethyl, methylsulphinyl or methylsulphonyl, or
A represents a radical of the formula

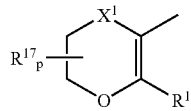 where

R$^{16}$ represents methyl, ethyl, trifluoromethyl, difluoromethyl or trichloromethyl and
R$^{17}$ represents methyl or ethyl,
X$^{1}$ represents a sulphur atom, represents SO, SO$_2$ or CH$_2$ and
p represents 0, 1 or 2, where R$^{17}$ represents identical or different radicals if p represents 2, or
A represents a radical of the formula

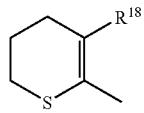 where

R$^{18}$ represents methyl, trifluoromethyl, difluoromethyl or trichloromethyl, or
A represents a radical of the formula

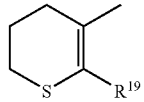 where

R$^{19}$ represents methyl, trifluoromethyl, difluoromethyl or trichloromethyl, or
A represents a radical of the formula

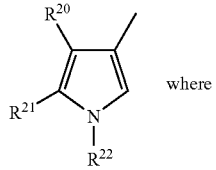 where

R$^{20}$ represents fluorine, chlorine, bromine, methyl, i-propyl, trifluoromethyl, difluoromethyl or trichloromethyl,
R$^{21}$ represents hydrogen, fluorine, chlorine, bromine, methyl, ethyl, trifluoromethyl, difluoromethyl or trichloromethyl and
R$^{22}$ represents hydrogen, methyl, ethyl, trifluoromethyl or methoxymethyl, or
A represents a radical of the formula

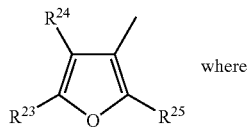 where

R$^{23}$ and R$^{24}$ independently of one another represent hydrogen, fluorine, chlorine, bromine, methyl, trifluoromethyl, difluoromethyl or trichloromethyl and
R$^{25}$ represents hydrogen, fluorine, chlorine, bromine, methyl, trifluoromethyl, difluoromethyl or trichloromethyl, or
A represents a radical of the formula

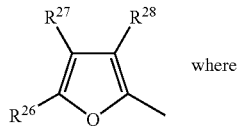 where

R$^{26}$ and R$^{27}$ independently of one another represent hydrogen, fluorine, chlorine, bromine, methyl, trifluoromethyl, difluoromethyl or trichloromethyl and
R$^{28}$ represents hydrogen, fluorine, chlorine, bromine, methyl, trifluoromethyl, difluoromethyl or trichloromethyl, or A represents a radical of the formula

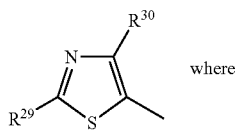
where

R²⁹ represents hydrogen, fluorine, chlorine, bromine, amino, methylamino, dimethylamino, methyl, trifluoromethyl, difluoromethyl or trichloromethyl and R³⁰ represents fluorine, chlorine, bromine, methyl, trifluoromethyl, difluoromethyl or trichloromethyl, or A represents a radical of the formula

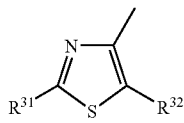
where

R³¹ represents hydrogen, fluorine, chlorine, bromine, amino, methylamino, dimethylamino, methyl, trifluoromethyl, difluoromethyl or trichloromethyl and R³² represents fluorine, chlorine, bromine, methyl, trifluoromethyl, difluoromethyl or trichloromethyl, or A represents a radical of the formula

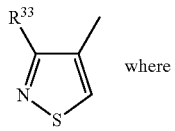
where

R³³ represents fluorine, chlorine, bromine, methyl, trifluoromethyl, difluoromethyl or trichloromethyl, or A represents a radical of the formula

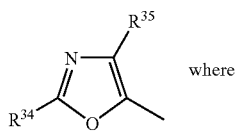

R³⁴ represents hydrogen, methyl or ethyl and
R³⁵ represents fluorine, chlorine, bromine, methyl or ethyl, or A represents a radical of the formula

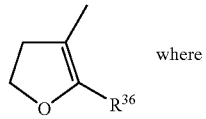
where

R³⁶ represents methyl, trifluoromethyl, difluoromethyl or trichloromethyl, or

A represents a radical of the formula

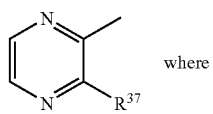
where

R³⁷ represents hydrogen, fluorine, chlorine, bromine or methyl.

Especially preferred are biphenylcarboxamides of the formula (I) in which $R^1$ represents hydrogen, fluorine, chlorine, methyl, $R^2$ represents hydrogen, m represents 1 or 2, where $R^1$ represents identical or different radicals if m represents 2, n represents 1, $R^3$ represents hydrogen, Y represents —$CH_2$—, —$(CH_2)_2$—, —$CF_2$— or —$(CF_2)_2$—, and A represents a radical of the formula

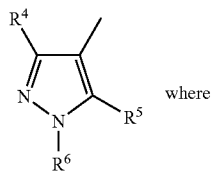
where $R^4$ represents methyl, monofluoromethyl, difluoromethyl or trifluoromethyl and $R^5$ represents hydrogen, fluorine, chlorine or methyl and $R^6$ represents methyl, or A represents a radical of the formula

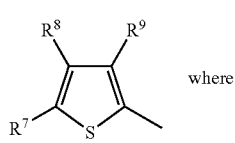
where $R^7$ and $R^8$ represent hydrogen and
$R^9$ represents methyl, or A represents a radical of the formula

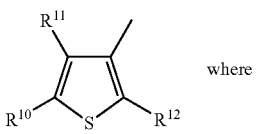

where $R^{10}$ and $R^{11}$ represent hydrogen and
$R^{12}$ represents methyl, or
A represents a radical of the formula

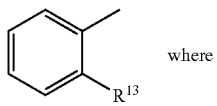

where $R^{13}$ represents iodine, methyl, difluoromethyl or trifluoromethyl, or
A represents a radical of the formula

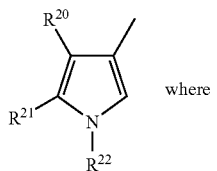

where $R^{20}$ represents methyl, trifluoromethyl or difluoromethyl,
$R^{21}$ represents hydrogen, fluorine, chlorine, methyl, trifluoromethyl or difluoromethyl and
$R^{22}$ represents hydrogen, methyl, ethyl, trifluoromethyl or methoxymethyl, or
A represents a radical of the formula

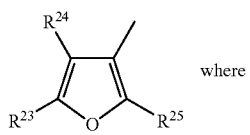

where $R^{23}$ and $R^{24}$ represent hydrogen and
$R^{25}$ represents methyl, or
A represents a radical of the formula

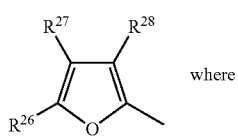

where $R^{26}$ and $R^{27}$ represent hydrogen and
$R^{28}$ represents methyl, or
A represents a radical of the formula

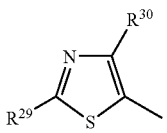

where $R^{29}$ represents amino, methylamino, dimethylamino, methyl or trifluoromethyl and
$R^{30}$ represents methyl, trifluoromethyl or difluoromethyl, or
A represents a radical of the formula

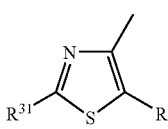

where $R^{31}$ represents amino, methylamino, dimethylamino, methyl or trifluoromethyl and
$R^{32}$ represents methyl, trifluoromethyl or difluoromethyl, or
A represents a radical of the formula

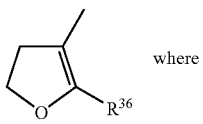

where $R^{36}$ represents methyl or trifluoromethyl.

Moreover, emphasis is given to compounds of the formula (I) in which $R^3$ represents hydrogen.

Moreover, emphasis is given to compounds of the formula (I) in which $R^2$ represents hydrogen.

Moreover, emphasis is given to compounds of the formula (I) in which Y represents —$CH_2$—, —$(CH_2)_2$—, —$CF_2$— or —$(CF_2)_2$—.

Moreover, emphasis is given to compounds of the formula (I) in which $R^1$ represents hydrogen, fluorine, chlorine or methyl and especially hydrogen or fluorine.

Moreover, emphasis is given to compounds of the formula (I) in which m represents 0, 1 or 2.

Moreover, emphasis is given to compounds of the formula (I) in which A represents a radical of the formula

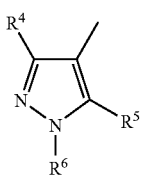

where $R^4$, $R^5$ and $R^6$ are as defined above.

Moreover, emphasis is given to compounds of the formula (I) in which A represents a radical of the formula

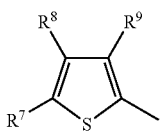

where $R^7$, $R^8$ and $R^9$ are as defined above.

Moreover, emphasis is given to compounds of the formula (I) in which A represents a radical of the formula

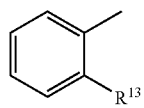

where $R^{13}$ is as defined above.

Moreover, emphasis is given to compounds of the formula (I) in which A represents a radical of the formula

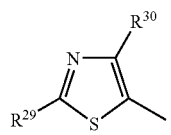

where $R^{29}$ and $R^{30}$ are as defined above.

Moreover, emphasis is given to compounds of the formula (I) in which A represents a radical of the formula

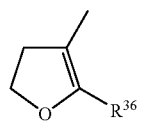

where $R^{36}$ is as defined above.

Saturated or unsaturated hydrocarbon radicals, such as alkyl or alkenyl, can in each case be straight-chain or branched as far as this is possible, even in combination with heteroatoms, such as, for example, in alkoxy.

Optionally substituted radicals can be mono- or polysubstituted, where in the case of polysubstitutions the substituents can be identical or different.

Halogen-substituted radicals, such as, for example, haloalkyl, are mono- or polyhalogenated. In the case of polyhalogenation, the halogen atoms can be identical or different. Here, halogen represents fluorine, chlorine, bromine and iodine, in particular fluorine, chlorine and bromine.

However, the general or preferred radical definitions or illustrations listed above can also be combined with one another as desired, i.e. including combinations between the respective ranges and preferred ranges. They apply to the end products and, correspondingly, to precursors and intermediates. Moreover, individual definitions may not apply.

Using 2-methyl-4-trifluoromethyl-1,3-thiazole-5-carbonyl chloride and (2,2-difluoro-1,3-benzodioxol-5-yl)phenylamine as starting materials, the course of the process (a) according to the invention can be illustrated by the formula scheme below.

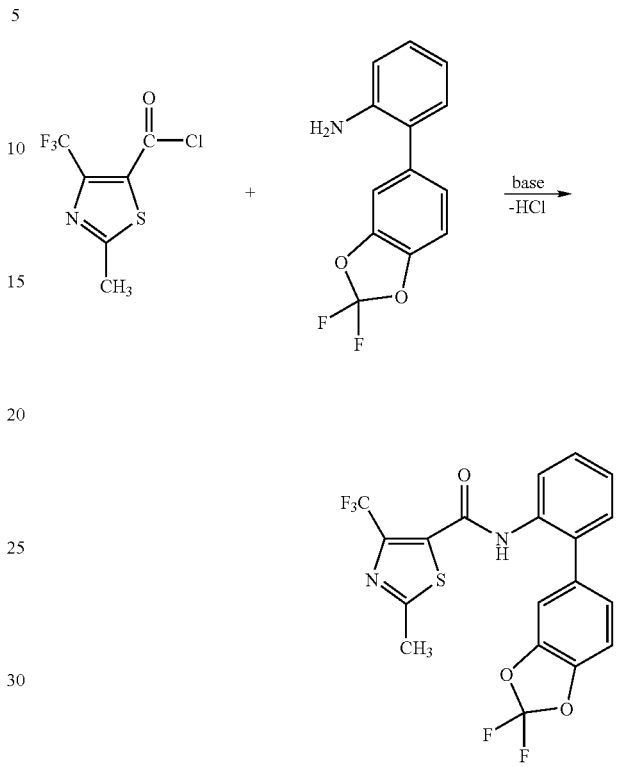

Using N-(2-bromophenyl)-5-fluoro-1,3-dimethyl-1H-pyrazole-4-carboxamide and 2,2,3,3-tetrafluoro-2,3-dihydro-1,4-benzodioxin-6-ylboronic acid as starting materials and a catalyst, the course of the process (b) according to the invention can be illustrated by the formula scheme below.

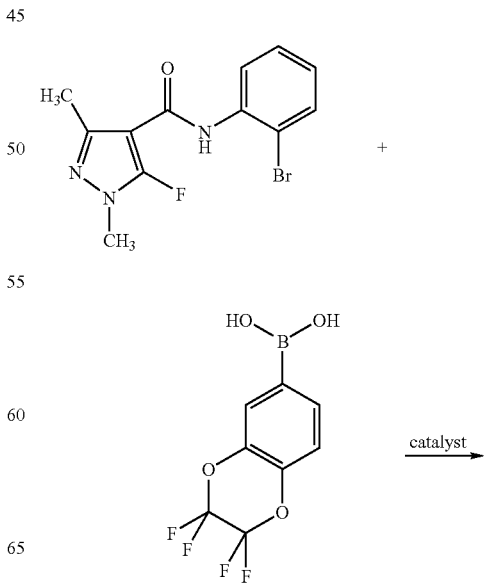

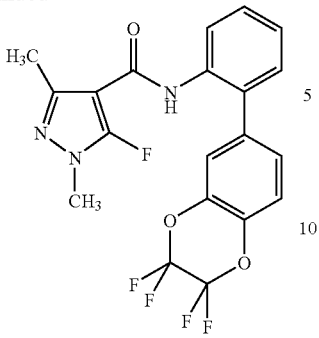

Using 2-{[(5-fluoro-1,3-dimethyl-1H-pyrazol-4-yl)carbonyl]amino}phenylboronic acid and 6-bromo-2,2,3,3-tetrafluoro-2,3-dihydro-1,4-benzodioxine as starting materials and a catalyst, the course of the process (c) according to the invention can be illustrated by the formula scheme below.

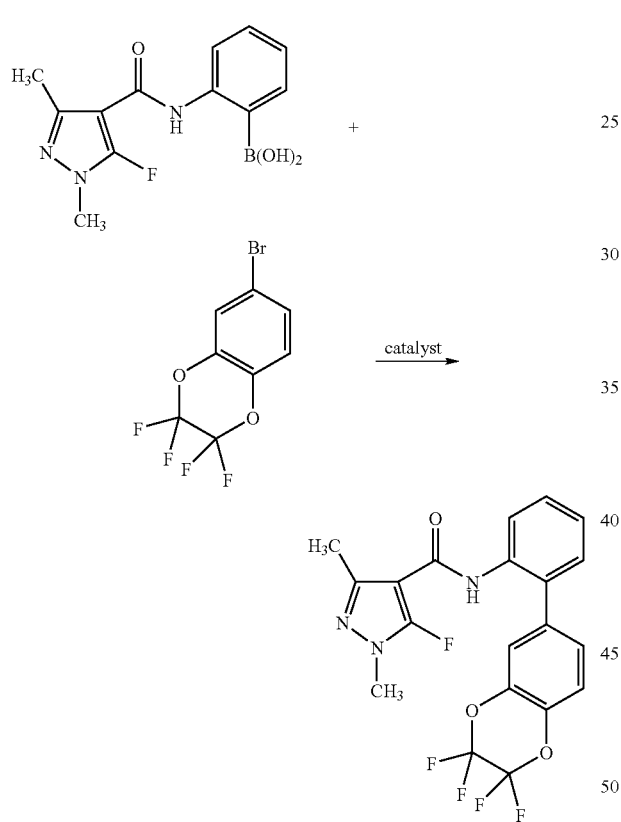

Using N-(2-bromophenyl)-5-fluoro-1,3-dimethyl-1H-pyrazole-4-carboxamide and 6-bromo-2,2,3,3-tetrafluoro-2,3-dihydro-1,4-benzodioxine as starting materials and a catalyst and 4,4,4',4',5,5,5,5'-octamethyl-2,2'-bis-1,3,2-dioxaborolane, the course of the process (d) according to the invention can be illustrated by the formula scheme below.

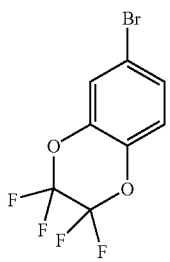

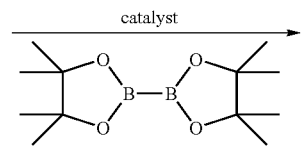

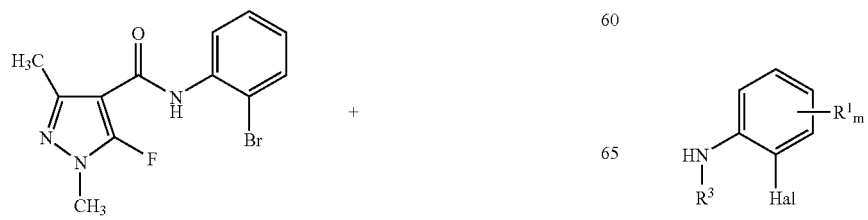

Explanation of the Processes and Intermediates

The formula (II) provides a general definition of the carboxylic acid derivatives required as starting materials for carrying out the process (a) according to the invention. In this formula, A preferably has those meanings which have already been mentioned in connection with the description of the compounds of the formula (I) according to the invention as being preferred, particularly preferred, very particularly preferred or especially preferred for these radicals. G preferably represents chlorine, bromine, hydroxyl, methoxy or ethoxy, particularly preferably chlorine, hydroxy or methoxy.

The carboxylic acid derivatives of the formula (II) are known or can be prepared by known processes (cf. WO 93/11 117, EP-A 0 545 099, EP-A 0 589 301 and EP-A 0 589 313).

The formula (III) provides a general definition of the aniline derivatives required as reaction components for carrying out the process (a) according to the invention. In this formula, $R^1$, $R^2$, m, n, $R^3$ and Y preferably have those meanings which have already been mentioned in connection with the description of the compounds of the formula (I) according to the invention as being preferred, particularly preferred, very particularly preferred or especially preferred for these radicals or these indices.

The aniline derivatives of the formula (III) are novel. Some of them can be prepared by known methods (cf. EP-A 0 545 099 and EP-A 0 589 301). Moreover, aniline derivatives of the formula (III) are obtained by e) reacting 2-haloaniline derivatives of the general formula (VIII)

(VIII)

in which
R¹, m and R³ are as defined above and
Hal represents halogen,
with boronic acid derivatives of the formula (V)

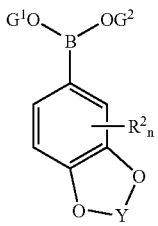

in which
R², n, Y, G¹ and G² are as defined above,
if appropriate in the presence of an acid binder, and if appropriate in the presence of an inert organic diluent, and if appropriate in the presence of a catalyst, or f) reacting anilineboronic acids of the formula (IX)

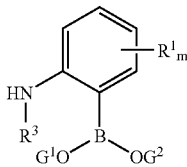

in which
R¹, m, R³, G¹ and G² are as defined above,
with phenyl derivatives of the formula (VII)

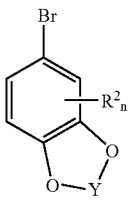

in which
R², n and Y are as defined above,
if appropriate in the presence of an acid binder, and if appropriate in the presence of an inert organic diluent, and if appropriate in the presence of a catalyst.

The formula (VIII) provides a general definition of the 2-haloaniline derivatives required as reaction components for carrying out the process (e) according to the invention. In this formula, R¹, m and R³ preferably have those meanings which have already been mentioned in connection with the description of the compounds of the formula (I) according to the invention as being preferred, particularly preferred, very particularly preferred or especially preferred for these radicals or these indices. Hal preferably represents fluorine, chlorine or bromine, particularly preferably chlorine or bromine.

The 2-haloaniline derivatives of the formula (VIII) are known and/or can be prepared from the corresponding nitro compounds by reduction. If R³ does not represent hydrogen, the compounds of the formula (VIII) can be obtained by known derivatizations of the resulting aniline derivatives.

The boronic acid derivatives of the formula (V) furthermore required as starting materials for carrying out the process (e) according to the invention are illustrated in more detail below, in connection with the process (b) according to the invention.

The formula (IX) provides a general definition of the anilineboronic acids required as reaction components for carrying out the process (f) according to the invention. In this formula, R¹, m and R³ preferably have those meanings which have already been mentioned in connection with the description of the compounds of the formula (I) according to the invention as being preferred, particularly preferred, very particularly preferred or especially preferred for these radicals or these indices. G¹ and G² preferably each represent hydrogen or together represent tetramethylethylene.

The anilineboronic acids of the formula (IX) are known and/or can be obtained by known methods.

The phenyl derivatives of the formula (VIII) furthermore required as starting materials for carrying out the process (f) according to the invention are illustrated in more detail below, in connection with the process (d) according to the invention.

The formula (IV) provides a general definition of the carboxamide derivatives required as starting materials for carrying out the process (b) and (d) according to the invention. In this formula, R¹, m, R³ and A preferably have those meanings which have already been mentioned in connection with the description of the compounds of the formula (I) according to the invention as being preferred, particularly preferred, very particularly preferred or especially preferred for these radicals or these indices.

The carboxamide derivatives of the formula (IV) are known or can be prepared by known processes (cf., for example, WO 91/01311, EP-A 0 371 950).

The formula (V) provides a general definition of the boronic acid derivatives required as starting materials for carrying out the processes (b) and (e) according to the invention. In this formula, R², n and Y preferably have those meanings which have already been mentioned in connection with the description of the compounds of the formula (I) according to the invention as being preferred, particularly preferred, very particularly preferred or especially preferred for these radicals or these indices. G¹ and G² preferably each represent hydrogen or together represent tetramethylethylene.

The boronic acid derivatives of the formula (V) are known and/or can be prepared by known processes (cf., for example, WO 01/90084 and U.S. Pat. No. 5,633,218). They are obtained, for example, by g) reacting phenyl derivatives of the formula (VII)

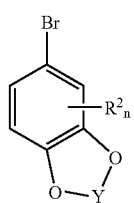

in which
R², n and Y are as defined above,
with boric acid esters of the formula (X)

$$B(OR^{38})_3 \qquad (X)$$

in which
R³⁸ represents $C_1$–$C_4$-alkyl,
in the presence of magnesium, if appropriate in the presence of a diluent (for example tetrahydrofuran).

The formula (X) provides a general definition of the boric acid esters required as reaction components for carrying out the process (g) according to the invention. In this formula, R³⁸ preferably represents methyl, ethyl, n- or i-propyl, particularly preferably methyl or ethyl.

The boric acid esters of the formula (X) are known chemicals for synthesis.

The formula (VI) provides a general definition of the carboxamide boronic acid derivatives required as reaction components for carrying out the process (c) according to the invention. In this formula, R¹, m, R³ and A preferably have those meanings which have already been mentioned in connection with the description of the compounds of the formula (I) according to the invention as being preferred, particularly preferred, very particularly preferred or especially preferred for these radicals or these indices. G¹ and G² preferably each represent hydrogen or together represent tetramethylethylene.

The carboxamide boronic acid derivatives of the formula (VI) are known and/or can be prepared by known processes.

The formula (VII) provides a general definition of the phenyl derivatives required as starting materials for carrying out the processes (c), (d), (f) and (g) according to the invention. In this formula, R², n and Y preferably have those meanings which have already been mentioned in connection with the description of the compounds of the formula (I) according to the invention as being preferred, particularly preferred, very particularly preferred or especially preferred for these radicals or these indices.

The phenyl derivatives of the formula (VII) are known or can be prepared by known processes (cf. Synth. Commun. 2000, 30, 665–669, Synth. Commun. 1999, 29, 1697–1701).

Suitable acid binders for carrying out the processes (a), (b), (c), (d), (e) and (f) according to the invention are in each case all inorganic and organic bases customary for such reactions. Preference is given to using alkaline earth metal or alkali metal hydroxides, such as sodium hydroxide, calcium hydroxide, potassium hydroxide, or else ammonium hydroxide, alkali metal carbonates, such as sodium carbonate, potassium carbonate, potassium bicarbonate, sodium bicarbonate, alkali metal or alkaline earth metal acetates, such as sodium acetate, potassium acetate, calcium acetate, and also tertiary amines, such as trimethylamine, triethylamine, tributylamine, N,N-dimethylaniline, pyridine, N-methylpiperidine, N,N-dimethylaminopyridine, diazabicyclooctane (DABCO), diazabicyclononene (DBN) or diazabicycloundecene (DBU). However, it is also possible to work in the absence of an additional acid binder, or to employ an excess of the amine component so that it simultaneously acts as acid binder.

Suitable diluents for carrying out the processes (a), (b), (c), (d), (e) and (f) according to the invention are in each case all customary inert organic solvents. Preference is given to using optionally halogenated aliphatic, alicyclic or aromatic hydrocarbons, such as petroleum ether, hexane, heptane, cyclohexane, methylcyclohexane, benzene, toluene, xylene or decalin; chlorobenzene, dichlorobenzene, dichloromethane, chloroform, carbon tetrachloride, dichloroethane or trichloroethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate, sulphoxides, such as dimethylsulphoxide, or sulphones, such as sulpholane.

When carrying out the processes (a), (b), (c), (d), (e) and (f) according to the invention, the reaction temperatures can in each case be varied within a relatively wide range. In general, the processes are carried out at temperatures between 0° C. and 140° C., preferably between 10° C. and 120° C.

The processes (a), (b), (c), (d), (e) and (f) according to the invention are generally each carried out under atmospheric pressure. However, in each case it is also possible to operate under elevated or reduced pressure.

When carrying out the process (a) according to the invention, in general 1 mol or else an excess of aniline derivative of the formula (III) and from 1 to 3 mol of acid binder are employed per mole of acid halide of the formula (II). However, it is also possible to employ the reaction components in other ratios. Work-up is carried out by customary methods. In general, water is added to the reaction mixture and the organic phase is separated off and, after drying, concentrated under reduced pressure. The residue that remains may, if appropriate, be freed of any impurities that may still be present using customary methods, such as chromatography or recrystallization.

When carrying out the process (b) according to the invention, in general 1 mol or else an excess of boronic acid derivative of the formula (V) and from 1 to 5 mol of acid binder are employed per mole of carboxamide of the formula (IV). However, it is also possible to employ the reaction components in other ratios. Work-up is carried out by customary methods. In general, water is added to the reaction mixture and the precipitate is separated off and dried. The residue that remains may, if appropriate, be freed of any impurities that may still be present using customary methods, such as chromatography or recrystallization.

When carrying out the process (c) according to the invention, in general 1 mol or else an excess of phenyl derivative of the formula (VII) and from 1 to 10 mol of acid binder and from 0.5 to 5 mol % of a catalyst are employed per mole of carboxamide boronic acid derivative of the formula (VI). However, it is also possible to employ the reaction components in other ratios. Work-up is carried out by customary methods. In general, water is added to the reaction mixture and the precipitate is separated off and dried. The residue that remains may, if appropriate, be freed of any impurities that may still be present using customary methods, such as chromatography or recrystallization.

When carrying out the process (d) according to the invention, in general 1 mol or else an excess of phenyl derivative of the formula (VII) and from 1 to 5 mol of acid binder and from 1 to 5 mol of a catalyst are employed per mole of carboxamide derivative of the formula (IV). However, it is also possible to employ the reaction components in other ratios. Work-up is carried out by customary methods. In general, water is added to the reaction mixture and the precipitate is separated off and dried. The residue that remains may, if appropriate, be freed of any impurities that may still be present using customary methods, such as chromatography or recrystallization.

The substances according to the invention have potent microbicidal activity and can be employed for controlling unwanted microorganisms, such as fungi and bacteria, in crop protection and in the protection of materials.

Fungicides can be employed in crop protection for controlling Plasmodiophoromycetes, Oomycetes, Chytridiomycetes, Zygomycetes, Ascomycetes, Basidiomycetes and Deuteromycetes.

Bactericides can be employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above may be mentioned as examples, but not by way of limitation:

Xanthomonas species, such as, for example, *Xanthomonas campestris* pv. *oryzae*;
Pseudomonas species, such as, for example, *Pseudomonas syringae* pv. *lachrymans*;
Erwinia species, such as, for example, *Erwinia amylovora*;
Pythium species, such as, for example, *Pythium ultimum*;
Phytophthora species, such as, for example, *Phytophthora infestans*;
Pseudoperonospora species, such as, for example, *Pseudoperonospora humuli* or *Pseudoperonospora cubensis*;
Plasmopara species, such as, for example, *Plasmopara viticola*;
Bremia species, such as, for example, *Bremia lactucae*;
Peronospora species, such as, for example, *Peronospora pisi* or *P. brassicae*;
Erysiphe species, such as, for example, *Erysiphe graminis*;
Sphaerotheca species, such as, for example, *Sphaerotheca fuliginea*;
Podosphaera species, such as, for example, *Podosphaera leucotricha*;
Venturia species, such as, for example, *Venturia inaequalis*;
Pyrenophora species, such as, for example, *Pyrenophora teres* or *P. graminea* (conidia form: *Drechslera*, syn: *Helminthosporium*);
Cochliobolus species, such as, for example, *Cochliobolus sativus* (conidia form: *Drechslera*, syn: *Helminthosporium*);
Uromyces species, such as, for example, *Uromyces appendiculatus*;
Puccinia species, such as, for example, *Puccinia recondita*;
Sclerotinia species, such as, for example, *Sclerotinia sclerotiorum*;
Tilletia species, such as, for example, *Tilletia caries*;
Ustilago species, such as, for example, *Ustilago nuda* or *Ustilago avenae*;
Pellicularia species, such as, for example, *Pellicularia sasakii*;
Pyricularia species, such as, for example, *Pyricularia oryzae*;
Fusarium species, such as, for example, *Fusarium culmorum*;
Botrytis species, such as, for example, *Botrytis cinerea*;
Septoria species, such as, for example, *Septoria nodorum*;
Leptosphaeria species, such as, for example, *Leptosphaeria nodorum*;
Cercospora species, such as, for example, *Cercospora canescens*;
Alternaria species, such as, for example, *Alternaria brassicae*; and
Pseudocercosporella species, such as, for example, *Pseudocercosporella herpotrichoides*.

The active compounds according to the invention also show a strong invigorating action in plants. Accordingly, they are suitable for mobilizing the internal defences of the plant against attack by unwanted microorganisms.

In the present context, plant-invigorating (resistance-inducing) compounds are to be understood as meaning substances which are capable of stimulating the defence system of plants such that, when the treated plants are subsequently inoculated with unwanted microorganisms, they display substantial resistance to these microorganisms.

In the present case, unwanted microorganisms are to be understood as meaning phytopathogenic fungi, bacteria and viruses. The compounds according to the invention can thus be used to protect plants within a certain period of time after treatment against attack by the pathogens mentioned. The period of time for which this protection is achieved generally extends for 1 to 10 days, preferably 1 to 7 days, from the treatment of the plants with the active compounds.

The fact that the active compounds are well tolerated by plants at the concentrations required for controlling plant diseases permits the treatment of above-ground parts of plants, of propagation stock and seeds, and of the soil.

The active compounds according to the invention are also suitable for increasing the yield of crops. In addition, they show reduced toxicity and are well tolerated by plants.

If appropriate, the active compounds according to the invention can, at certain concentrations and application rates, also be employed as herbicides, for regulating plant growth and for controlling animal pests. If appropriate, they can also be used as intermediates or precursors in the synthesis of other active compounds.

According to the invention, it is possible to treat all plants and parts of plants. Plants are to be understood here as meaning all plants and plant populations, such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including plant cultivars which can or cannot be protected by plant breeders' certificates. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. Parts of plants also include harvested material and vegetative and generative propagation material, for example seedlings, tubers, rhizomes, cuttings and seeds.

The treatment of the plants and parts of plants according to the invention with the active compounds is carried out directly or by action on their environment, habitat or storage area according to customary treatment methods, for example by dipping, spraying, evaporating, atomizing, broadcasting, brushing-on and, in the case of propagation material, in particular in the case of seeds, furthermore by one- or multilayer coating.

In the protection of materials, the compounds according to the invention can be employed for protecting industrial materials against infection with, and destruction by, unwanted microorganisms.

Industrial materials in the present context are understood as meaning non-living materials which have been prepared for use in industry. For example, industrial materials which are intended to be protected by active compounds according to the invention from microbial change or destruction can be tackifiers, sizes, paper and board, textiles, leather, wood, paints and plastic articles, cooling lubricants and other materials which can be infected with, or destroyed by, microorganisms. Parts of production plants, for example cooling-water circuits, which may be impaired by the proliferation of microorganisms may also be mentioned within the scope of the materials to be protected. Industrial materials which may be mentioned within the scope of the present invention are preferably tackifiers, sizes, paper and board, leather, wood, paints, cooling lubricants and heat-transfer liquids, particularly preferably wood.

Microorganisms capable of degrading or changing the industrial materials which may be mentioned are, for example, bacteria, fungi, yeasts, algae and slime organisms. The active compounds according to the invention preferably act against fungi, in particular moulds, wood-discolouring and wood-destroying fungi (Basidiomycetes) and against slime organisms and algae.

Microorganisms of the following genera may be mentioned as examples:
*Alternaria*, such as *Alternaria tenuis*,
*Aspergillus*, such as *Aspergillus niger*,
*Chaetomium*, such as *Chaetomium globosum*,
*Coniophora*, such as *Coniophora puetana*,
*Lentinus*, such as *Lentinus tigrinus*,
*Penicillium*, such as *Penicillium glaucum*,
*Polyporus*, such as *Polyporus versicolor*,
*Aureobasidium*, such as *Aureobasidium pullulans*,
*Sclerophoma*, such as *Sclerophoma pityophila*,
*Trichoderma*, such as *Trichoderma viride*,
*Escherichia*, such as *Escherichia coli*,
*Pseudomonas*, such as *Pseudomonas aeruginosa*, and
*Staphylococcus*, such as *Staphylococcus aureus*.

Depending on their particular physical and/or chemical properties, the active compounds can be converted into the customary formulations, such as solutions, emulsions, suspensions, powders, foams, pastes, granules, aerosols and microencapsulations in polymeric substances and in coating compositions for seeds, and ULV cool and warm fogging formulations.

These formulations are produced in a known manner, for example by mixing the active compounds with extenders, that is liquid solvents, liquefied gases under pressure, and/or solid carriers, optionally with the use of surfactants, that is emulsifiers and/or dispersants, and/or foam formers. If the extender used is water, it is also possible to employ, for example, organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide or dimethyl sulphoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as finely divided silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignosulphite waste liquors and methylcellulose.

Tackifiers such as carboxymethylcellulose, natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 percent by weight of active compound, preferably between 0.5 and 90%.

The active compounds according to the invention can, as such or in their formulations, also be used in a mixture with known fungicides, bactericides, acaricides, nematicides or insecticides, to broaden, for example, the activity spectrum or to prevent development of resistance. In many cases, synergistic effects are obtained, i.e. the activity of the mixture is greater than the activity of the individual components.

Suitable mixing components are, for example, the following compounds:

Fungicides:
2-phenylphenol; 8-hydroxyquinoline sulphate;
acibenzolar-5-methyl; aldimorph; amidoflumet; ampropylfos; ampropylfos-potassium; andoprim; anilazine; azaconazole; azoxystrobin;
benalaxyl; benodanil; benomyl; benthiavalicarb-isopropyl; benzamacril; benzamacrilisobutyl; bilanafos; binapacryl; biphenyl; bitertanol; blasticidin-S; bromuconazole; bupirimate; buthiobate; butylamine;
calcium polysulphide; capsimycin; captafol; captan; carbendazim; carboxin; carpropamid; carvone; chinomethionat; chlobenthiazone; chlorfenazole; chloroneb; chlorothalonil; chlozolinate; clozylacon; cyazofamid; cyflufenamid; cymoxanil; cyproconazole; cyprodinil; cyprofuram;
Dagger G; debacarb; dichlofluanid; dichlone; dichlorophen; diclocymet; diclomezine; dicloran; diethofencarb; difenoconazole; diflumetorim; dimethirimol; dimethomorph; dimoxystrobin; diniconazole; diniconazole-M; dinocap; diphenylamine; dipyrithione; ditalimfos; dithianon; dodine; drazoxolon;
edifenphos; epoxiconazole; ethaboxam; ethirimol; etridiazole;
famoxadone; fenamidone; fenapanil; fenarimol; fenbuconazole; fenfuram; fenhexamid; fenitropan; fenoxanil; fenpiclonil; fenpropidin; fenpropimorph; ferbam; fluazinam; flubenzimine; fludioxonil; flumetover; flumorph; fluoromide; fluoxastrobin; fluquinconazole; flurprimidol; flusilazole; flusulphamide; flutolanil; flutriafol; folpet; fosetyl-Al; fosetyl-sodium; fuberidazole; furalaxyl; furametpyr; furcarbanil; furmecyclox;
guazatine; hexachlorobenzene; hexaconazole; hymexazole; imazalil; imibenconazole; iminoctadine triacetate; iminoctadine tris(albesil); iodocarb; ipconazole; iprobenfos; iprodione; iprovalicarb; irumamycin; isoprothiolane; isovaledione;
kasugamycin; kresoxim-methyl;
mancozeb; maneb; meferimzone; mepanipyrim; mepronil; metalaxyl; metalaxyl-M; metconazole; methasulphocarb; methfuroxam; metiram; metominostrobin; metsulphovax; mildiomycin; myclobutanil; myclozolin;

natamycin; nicobifen; nitrothal-isopropyl; noviflumuron; nuarimol;

ofurace; orysastrobin; oxadixyl; oxolinic acid; oxpoconazole; oxycarboxin; oxyfenthiin;

paclobutrazole; pefurazoate; penconazole; pencycuron; phosdiphen; phthalide; picoxystrobin; piperalin; polyoxins; polyoxorim; probenazole; prochloraz; procymidone; propamocarb; propanosine-sodium; propiconazole; propineb; proquinazid; prothioconazole; pyraclostrobin; pyrazophos; pyrifenox; pyrimethanil; pyroquilon; pyroxyfur; pyrrolenitrine;

quinconazole; quinoxyfen; quintozene; simeconazole; spiroxamine; sulphur; tebuconazole; tecloftalam; tecnazene; tetcyclacis; tetraconazole; thiabendazole; thicyofen; thifluzamide; thiophanate-methyl; thiram; tioxymid; tolclofos-methyl; tolylfluanid; triadimefon; triadimenol; triazbutil; triazoxide; tricyclamide; tricyclazole; tridemorph; trifloxystrobin; triflumizole; triforine; triticonazole;

uniconazole; validamycin A; vinclozolin; zineb; ziram; zoxamide;

(2S)-N-[2-[4-[[3-(4-chlorophenyl)-2-propynyl]oxy]-3-methoxyphenyl]ethyl]-3-methyl-2-[(methylsulphonyl)amino]butanamide;

1-(1-naphthalenyl)-1H-pyrrole-2,5-dione;

2,3,5,6-tetrachloro-4-(methylsulphonyl)pyridine;

2-amino-4-methyl-N-phenyl-5-thiazolecarboxamide;

2-chloro-N-(2,3-dihydro-1,1,3-trimethyl-1H-inden-4-yl)-3-pyridinecarboxamide;

3,4,5-trichloro-2,6-pyridinedicarbonitrile;

actinovate; cis-1-(4-chlorophenyl)-2-(1H-1,2,4-triazol-1-yl)cycloheptanol;

methyl 1-(2,3-dihydro-2,2-dimethyl-1H-inden-1-yl)-1H-imidazole-5-carboxylate;

monopotassium carbonate;

N-(6-methoxy-3-pyridinyl)-cyclopropanecarboxamide;

N-butyl-8-(1,1-dimethylethyl)-1-oxaspiro[4.5]decane-3-amine;

sodium tetrathiocarbonate;

and copper salts and preparations, such as Bordeaux mixture; copper hydroxide; copper naphthenate; copper oxychloride; copper sulphate; cufraneb; copper oxide; mancopper; oxine-copper.

Bactericides:

bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:

abamectin, ABG-9008, acephate, acequinocyl, acetamiprid, acetoprole, acrinathrin, AKD-1022, AKD-3059, AKD-3088, alanycarb, aldicarb, aldoxycarb, allethrin, allethrin 1R-isomers, alpha-cypermethrin (alphamethrin), amidoflumet, aminocarb, amitraz, avermectin, AZ-60541, azadirachtin, azamethiphos, azinphos-methyl, azinphosethyl, azocyclotin,

*Bacillus popilliae, Bacillus sphaericus, Bacillus subtilis, Bacillus thuringiensis, Bacillus thuringiensis* strain EG-2348, *Bacillus thuringiensis* strain GC-91, *Bacillus thuringiensis* strain NCTC-11821, baculoviruses, *Beauveria bassiana, Beauveria tenella*, bendiocarb, benfuracarb, bensultap, benzoximate, beta-cyfluthrin, beta-cypermethrin, bifenazate, bifenthrin, binapacryl, bioallethrin, bioallethrin-5-cyclopentylisomer, bioethanomethrin, biopermethrin, bioresmethrin, bistrifluron, BPMC, brofenprox, bromophos-ethyl, bromopropylate, bromfenvinfos (-methyl), BTG-504, BTG-505, bufencarb, buprofezin, butathiofos, butocarboxim, butoxycarboxim, butylpyridaben, cadusafos, camphechlor, carbaryl, carbofuran, carbophenothion, carbosulphan, cartap, CGA-50439, chinomethionat, chlordane, chlordimeform, chloethocarb, chlorethoxyfos, chlorfenapyr, chlorfenvinphos, chlorfluazuron, chlormephos, chlorobenzilate, chloropicrin, chlorproxyfen, chlorpyrifos-methyl, chlorpyrifos (-ethyl), chlovaporthrin, chromafenozide, cis-cypermethrin, cis-resmethrin, cis-permethrin, clocythrin, cloethocarb, clofentezine, clothianidin, clothiazoben, codlemone, coumaphos, cyanofenphos, cyanophos, cyprene, cyprothrin, *Cydia pomonella*, cyfluthrin, cyhalothrin, cyhexatin, cypermethrin, cyphenothrin (1R-trans-isomer), cyromazine, DDT, deltamethrin, demeton-5-methyl, demeton-5-methylsulphone, diafenthiuron, dialifos, diazinon, dichlofenthion, dichlorvos, dicofol, dicrotophos, dicyclanil, diflubenzuron, dimethoate, dimethylvinphos, dinobuton, dinocap, dinotefuran, diofenolan, disulphoton, docusatsodium, dofenapyn, DOWCO-439, eflusilanate, emamectin, emamectin-benzoate, empenthrin (1R-isomer), endosulphan, *Entomopthora* spp., EPN, esfenvalerate, ethiofencarb, ethiprole, ethion, ethoprophos, etofenprox, etoxazole, etrimfos, famphur, fenamiphos, fenazaquin, fenbutatin oxide, fenfluthrin, fenitrothion, fenobucarb, fenothiocarb, fenoxacrim, fenoxycarb, fenpropathrin, fenpyrad, fenpyrithrin, fenpyroximate, fensulphothion, fenthion, fentrifanil, fenvalerate, fipronil, flonicamid, fluacrypyrim, fluazuron, flubenzimine, flubrocythrinate, flucycloxuron, flucythrinate, flufenerim, flufenoxuron, flufenprox, flumethrin, flupyrazofos, flutenzin (flufenzine), fluvalinate, fonofos, formetanate, formothion, fosmethilan, fosthiazate, fubfenprox (fluproxyfen), furathiocarb, gamma-HCH, gossyplure, grandlure, granulosis viruses, halfenprox, halofenozide, HCH, HCN-801, heptenophos, hexaflumuron, hexythiazox, hydramethylnone, hydroprene, IKA-2002, imidacloprid, imiprothrin, indoxacarb, iodofenphos, iprobenfos, isazofos, isofenphos, isoprocarb, isoxathion, ivermectin, japonilure, kadethrin, nuclear polyhedrosis viruses, kinoprene, lambda-cyhalothrin, lindane, lufenuron, malathion, mecarbam, mesulphenfos, metaldehyde, metamsodium, methacrifos, methamidophos, *Metharhizium anisopliae, Metharhizium flavoviride*, methidathion, methiocarb, methomyl, methoprene, methoxychlor, methoxyfenozide, metolcarb, metoxadiazone, mevinphos, milbemectin, milbemycin, MKI-245, MON-45700, monocrotophos, moxidectin, MTI-800, naled, NC-104, NC-170, NC-184, NC-194, NC-196, niclosamide, nicotine, nitenpyram, nithiazine, NNI-0001, NNI-0101, NNI-0250, NNI-9768, novaluron, noviflumuron, OK-5101, OK-5201, OK-9601, OK-9602, OK-9701, OK-9802, omethoate, oxamyl, oxydemeton-methyl, Paecilomyces fumosoroseus, parathion-methyl, parathion (-ethyl), permethrin (cis-, trans-), petroleum, PH-6045, phenothrin (1R-trans isomer), phenthoate, phorate, phosalone, phosmet, phosphamidon, phosphocarb, phoxim, piperonyl butoxide, pirimicarb, pirimiphos-methyl, pirimiphos-ethyl, prallethrin, profenofos, promecarb, propaphos, propargite, propetamphos, propoxur, prothiofos, prothoate, protrifenbute, pymetrozine, pyraclofos, pyresmethrin, pyrethrum, pyridaben, pyridalyl, pyridaphenthion, pyridathion, pyrimidifen, pyriproxyfen, quinalphos, resmethrin, RH-5849, ribavirin, RU-12457, RU-15525, S-421, S-1833, salithion, sebufos, SI-0009, silafluofen, spinosad, spirodiclofen, spiromesifen, sulphlurarnid, sulphotep, sulprofos, SZI-121, tau-fluvalinate, tebufenozide, tebufenpyrad, tebupirimfos, teflubenzuron, tefluthrin, temephos, temivinphos, terbam, terbufos, tetrachlorvinphos, tetradifon, tetramethrin, tetramethrin (1R-isomer), tetrasul, theta-cypermethrin, thiacloprid, thiamethoxam, thiapronil, thiatriphos, thiocyclam hydrogenoxalate, thiodicarb, thiofanox, thiometon, thiosultap-sodium, thuringiensin, tolfenpyrad, tralocythrin, tralomethrin, transfluthrin, triarathene, triazamate, triazophos, triazuron, trichlophenidine, trichlorfon, triflumuron, trimethacarb, vamidothion, vaniliprole, verbutin, *Verticillium lecanii*, WL-108477, WL-40027, YI-5201, YI-5301, YI-5302, XMC, xylylcarb, ZA-3274, zeta-cypermethrin, zolaprofos, ZXI-8901, the compound 3-methylphenyl propylcarbamate (tsumacide Z), the compound 3-(5-chloro-3-pyridinyl)-8-(2,2,2-trifluoroethyl)-8-azabicyclo[3.2.1]-octane-3-carbonitrile (CAS-Reg. No. 185982-80-3) and the corresponding 3-endoisomer (CAS-Reg. No. 185984-60-5) (cf. WO-96/37494, WO-98/25923), and preparations which comprise insecticidally active plant extracts, nematodes, fungi or viruses.

A mixture with other known active compounds, such as herbicides, or with fertilizers and growth regulators, safeners and/or semiochemicals is also possible.

In addition, the compounds of the formula (I) according to the invention also have very good antimycotic activity. They have a very broad antimycotic activity spectrum in particular against dermatophytes and yeasts, moulds and diphasic fungi (for example against *Candida* species such as *Candida albicans, Candida glabrata*) and *Epidermophyton floccosum, Aspergillus* species such as *Aspergillus niger* and *Aspergillus fumigatus, Trichophyton* species such as *Trichophyton mentagrophytes, Microsporon* species such as *Microsporon canis* and *audouinii*. The list of these fungi does by no means limit the mycotic spectrum which can be covered, but is only for illustration.

The active compounds can be used as such, in the form of their formulations or the use forms prepared therefrom, such as ready-to-use solutions, suspensions, wettable powders, pastes, soluble powders, dusts and granules. Application is carried out in a customary manner, for example by watering, spraying, atomizing, broadcasting, dusting, foaming, spreading, etc. It is furthermore possible to apply the active compounds by the ultra-low volume method, or to inject the active compound preparation or the active compound itself into the soil. It is also possible to treat the seeds of the plants.

When using the active compounds according to the invention as fungicides, the application rates can be varied within a relatively wide range, depending on the kind of application. For the treatment of parts of plants, the active compound application rates are generally between 0.1 and 10,000 g/ha, preferably between 10 and 1000 g/ha. For seed dressing, the active compound application rates are generally between 0.001 and 50 g per kilogram of seed, preferably between 0.01 and 10 g per kilogram of seed. For the treatment of the soil, the active compound application rates are generally between 0.1 and 10,000 g/ha, preferably between 1 and 5,000 g/ha.

As already mentioned above, it is possible to treat all plants and their parts according to the invention. In a preferred embodiment, wild plant species and plant cultivars, or those obtained by conventional biological breeding, such as crossing or protoplast fusion, and parts thereof, are treated. In a further preferred embodiment, transgenic plants and plant cultivars obtained by genetic engineering, if appropriate in combination with conventional methods (Genetically Modified Organisms), and parts thereof, are treated. The term "parts" or "parts of plants" or "plant parts" has been explained above.

Particularly preferably, plants of the plant cultivars which are in each case commercially available or in use are treated according to the invention. Plant cultivars are to be understood as meaning plants having new properties ("traits") and which have been obtained by conventional breeding, by mutagenesis or by recombinant DNA techniques. They can be cultivars, varieties, bio- or genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

The transgenic plants or plant cultivars (i.e. those obtained by genetic engineering) which are preferably to be treated according to the invention include all plants which, in the genetic modification, received genetic material which imparted particularly advantageous useful properties ("traits") to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are emphasized are in particular increased defence of the plants against insects by toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (hereinbelow referred to as "Bt plants"). Traits that are also particularly emphasized are the increased defence of the plants against fungi, bacteria and viruses by systemic acquired resistance (SAR), systemin, phytoalexins, elicitors and resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), Star-Link® (for example maize), Bollgard® (cotton), Nucoton® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned also include the varieties sold under the name Clearfield® (for example maize). Of course, these statements also apply to plant cultivars which have these genetic traits or genetic traits still to be developed, and which will be developed and/or marketed in the future.

The plants listed can be treated according to the invention in a particularly advantageous manner with the compounds of the general formula (I) or the active compound mixtures according to the invention. The preferred ranges stated above for the active compounds or mixtures also apply to the treatment of these plants. Particular emphasis is given to the treatment of plants with the compounds or mixtures specifically mentioned in the present text.

The preparation and the use of the active compounds according to the invention is illustrated by the examples below.

PREPARATION EXAMPLES

Example 1

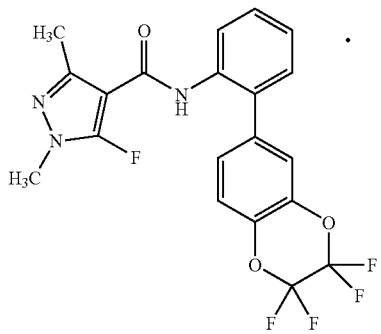

9.77 g of cesium carbonate and 2 ml of water are added to a solution of 3.12 g of N-(2-bromophenyl)-5-fluoro-1,3-dimethyl-1H-pyrazole-4-carboxamide and 3.28 g of 2,2,3,3-tetrafluoro-2,3-dihydro-1,4-benzodioxin-6-ylboronic acid (V-1) in 10 ml of n-butanol. With stirring and under an atmosphere of argon, 60 mg of tetrakis-(triphenylphosphine)palladium(0) are added. The reaction mixture is stirred at 80° C. for 8 h. For work-up, the mixture is poured into water and extracted with ethyl acetate and the extract is dried and concentrated. The residue is chromatographed on silica gel (cyclohexane/ethyl acetate 2:1).

This gives 4.00 g (83% of theory) of 5-fluoro-1,3-dimethyl-N-[2-(2,2,3,3-tetrafluoro-2,3-dihydro-1,4-benzodioxin-6-yl)phenyl]-1H-pyrazole-4-carboxamide in the form of a colourless solid [logP (pH 2.3)=3.77].

Example 2

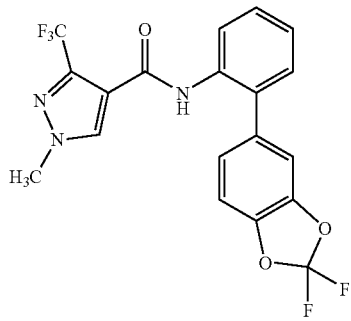

Under argon, 0.37 g (1.6 mmol) of 5-bromo-2,2-difluoro-1,3-benzodioxole, 0.4 g (1.6 mmol) of 4,4,4',4',5,5,5',5'-octamethyl-2,2'-bis-1,3,2-dioxaborolane and 0.42 g (4.3 mmol) of potassium acetate are suspended in 5 ml of dimethyl sulphoxide, and 0.05 g (0.07 mmol) of 1,1'-bis(diphenylphosphino)ferrocenepalladium(II) chloride is added. After 2 h at 80° C., the mixture is cooled to room temperature, and 0.51 g (1.3 mmol) of N-(2-iodophenyl)-1-methyl-3-(trifluoromethyl)-1H-pyrazol-4-carboxamide (IV-1), 3.25 ml of a 2 M solution of sodium carbonate and a further 0.05 g (0.07 mmol) of 1,1'-bis(diphenylphosphino)ferrocenepalladium(II) chloride are added. After 45 min at 70° C., the mixture is diluted with 5 ml of water and extracted 3 times with in each case 50 ml of ethyl acetate. The extracts are dried over sodium sulphate, filtered and concentrated under reduced pressure. The crude product is taken up in diethyl ether and chromatographed on silica gel (cyclohexane/ethyl acetate 3:1).

This gives 0.23 g (41% of theory) of N-[2-(2,2-difluoro-1,3-benzodioxol-5-yl)-phenyl]-1-methyl-3-(trifluoromethyl)-1H-pyrazol-4-carboxamide [logP (pH 2.3)=3.37].

The biphenylcarboxamides of the formula (I) listed in Table 1 below are likewise prepared analogously to Examples 1 and 2 described above and in accordance with the general descriptions of the processes.

TABLE 1

(I)

[Structure: N-acyl biphenyl with benzodioxole bearing Y bridge; substituents $R^1_m$, $R^2_n$, $R^3$, A]

| Ex. | $R^1_m$ | $R^2_n$ | $R^3$ | Y | A | logP (pH2.3) |
|---|---|---|---|---|---|---|
| 3 | H | H | H | —CF$_2$— | 2-(trifluoromethyl)phenyl | 3.94 |
| 4 | H | H | H | —CF$_2$— | 2-methyl-3-thienyl | 3.99 |
| 5 | H | H | H | —CF$_2$— | 4-(trifluoromethyl)-5-methyl-2-methylthiazol-yl | 3.81 |
| 6 | H | H | H | —(CF$_2$)$_2$— | 2-(trifluoromethyl)phenyl | 5.93 |
| 7 | H | H | H | —(CF$_2$)$_2$— | 2-methyl-3-methylfuryl | 4.08 |
| 8 | H | H | H | —(CF$_2$)$_2$— | 3-(trifluoromethyl)-4-methyl-1-methylpyrazol-5-yl | 3.85 |
| 9 | H | H | H | —(CF$_2$)$_2$— | 2-methyl-3-thienyl | 4.46 |

TABLE 1-continued (I)

[Structure: same as above]

| Ex. | $R^1_m$ | $R^2_n$ | $R^3$ | Y | A | logP (pH2.3) |
|---|---|---|---|---|---|---|
| 10 | H | H | H | —(CF$_2$)$_2$— | 4-(trifluoromethyl)-5-methyl-2-methylthiazol-yl | 3.94 |
| 11 | 4,5-F$_2$ | H | H | —CH$_2$— | 3-methyl-4-methyl-5-fluoro-1-methylpyrazol-yl | 3.24 |
| 12 | 4-Cl | H | H | —CH$_2$— | 3-methyl-4-methyl-5-fluoro-1-methylpyrazol-yl | 3.32 |
| 13 | 4-CH$_3$, 5-F | H | H | —CH$_2$— | 3-methyl-4-methyl-5-fluoro-1-methylpyrazol-yl | 3.37 |
| 14 | 5-CH$_3$ | H | H | —CH$_2$— | 3-methyl-4-methyl-5-fluoro-1-methylpyrazol-yl | 3.01 |
| 15 | 4,6-F$_2$ | H | H | —CH$_2$— | 3-methyl-4-methyl-5-fluoro-1-methylpyrazol-yl | 2.34 |

TABLE 1-continued

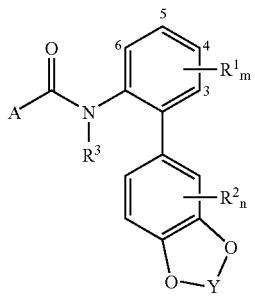

(I)

| Ex. | R¹ₘ | R²ₙ | R³ | Y | A | logP (pH2.3) |
|---|---|---|---|---|---|---|
| 16 | 4-CH₃ | H | H | —CH₂— | (pyrazole) | 3.10 |
| 17 | 4-F, 6-Cl | H | H | —CH₂— | (pyrazole) | 2.53 |
| 18 | 4-Cl, 6-F | H | H | —CH₂— | (pyrazole) | 2.74 |
| 19 | H | H | H | —CF₂— | (pyrazole) | 3.22 |
| 20 | H | H | H | —CH₂— | (furan) | 2.87 |
| 21 | H | H | Me | —(CF₂)₂— | (pyrazole) | 3.44 |

Preparation of Starting Materials of the Formula (IV)

Example (IV-1)

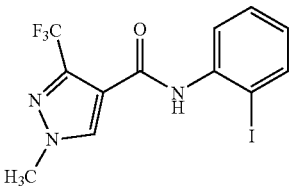

6.57 g (30.0 mmol) of 2-iodoaniline and 6.1 g (60.0 mmol) of triethylamine are dissolved in 100 ml of tetrahydrofuran and, at room temperature, 7.65 g (36.0 mmol) of 1-methyl-3-(trifluoromethyl)-1H-pyrazole-4-carbonyl chloride are added slowly. The reaction solution is heated at 50° C. for 16 h. For work-up, the mixture is concentrated under reduced pressure and the crude product is chromatographed on silica gel (cyclohexane/ethyl acetate 1:1).

This gives 10.0 g (85% of theory) of N-(2-iodophenyl)-1-methyl-3-(trifluoromethyl)-1H-pyrazole-4-carboxamide [logP (pH 2.3)=2.46].

Preparation of Starting Materials of the Formula (V)

Example (V-1)

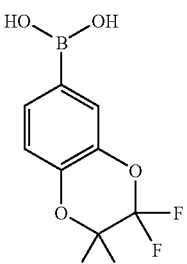

A few grains of iodine are added to a suspension of 4.86 g of magnesium turnings in 20 ml of tetrahydrofuran (anhydrous), and 57.4 g of 6-bromo-2,2,3,3-tetrafluoro-2,3-dihydro-1,4-benzodioxine in 60 ml of tetrahydrofuran are then added dropwise under an atmosphere of argon. By adjusting the rate of the dropwise addition, the exothermic reaction is maintained close to the boiling point. After the dropwise addition has ended, the mixture is stirred under reflux for 30 min and then cooled to room temperature. The solution of the Grignard reagent is, together with a solution of 29.2 g of triethyl borate in 60 ml of tetrahydrofuran, added dropwise, at −10° C. and over a period of 30 min, to 100 ml of tetrahydrofuran. The mixture is then stirred at −10° C. for another 1 h and then warmed to room temperature and stirred for another 30 min. For work-up, the reaction solution is, at −10° C., hydrolysed with 14 ml of water and adjusted to pH 4 using 80 ml of 10% strength sulphuric acid.

The mixture is extracted with diethyl ether and the aqueous phase is saturated with sodium chloride and extracted with diethyl ether. The combined ether phases are, together with 200 ml of water, concentrated. The solid residue is triturated with a little methylene chloride, filtered off with suction and dried.

This gives 47.3 g (75% of theory) of 2,2,3,3-tetrafluoro-2,3-dihydro-1,4-benzodioxin-6-yl-boronic acid [logP (pH 2.3)=2.49].

The logP values given in the Preparation Examples were determined in accordance with EEC Directive 79/831 Annex V.A8 by HPLC (High Performance Liquid Chromatography) using a reversed-phase column (C 18). Temperature: 43° C.

Mobile phases for the determination in the acidic range: 0.1% aqueous phosphoric acid, acetonitrile; linear gradient from 10% acetonitrile to 90% acetonitrile.

Calibration was carried out using unbranched alkan-2-ones (having 3 to 16 carbon atoms) with known logP values (determination of the logP values by the retention times using linear interpolation between two successive alkanones).

The lambda max values were determined in the maxima of the chromatographic signals using the UV spectra from 200 nm to 400 nm.

USE EXAMPLES

Example A

*Podosphaera* Test (Apple)/Protective

Solvents:
24.5 parts by weight of acetone
24.5 parts by weight of dimethylacetamide Emulsifier:
1.0 part by weight of alkylaryl polyglycol ether To produce a suitable preparation of active compound, 1 part by weight of active compound is mixed with the stated amounts of solvents and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of the apple mildew pathogen *Podosphaera leucotricha*. The plants are then placed in a greenhouse at about 23° C. and a relative atmospheric humidity of about 70%.

Evaluation is carried out 10 days after the inoculation. 0% means an efficacy which corresponds to that of the control, whereas an efficacy of 100% means that no infection is observed.

Active compounds, application rates and test results are shown in the table below.

TABLE A

Podosphaera test (apple)/protective

| Active compound | | Application rate of active compound in g/ha | Efficacy in % |
|---|---|---|---|
| 2 | [structure] | 100 | 100 |
| 3 | [structure] | 100 | 100 |
| 5 | [structure] | 100 | 100 |
| 6 | [structure] | 100 | 100 |

TABLE A-continued

Podosphaera test (apple)/protective

| Active compound | Application rate of active compound in g/ha | Efficacy in % |
|---|---|---|
| 9 (structure) | 100 | 100 |
| 10 (structure) | 100 | 100 |
| 19 (structure) | 100 | 100 |
| 1 (structure) | 100 | 100 |

Example B

*Sphaerotheca* Test (Cucumber)/Protective

Solvents:
 24.5 parts by weight of acetone
 24.5 parts by weight of dimethylacetamide Emulsifier:
 1.0 part by weight of alkylaryl polyglycol ether To produce a suitable preparation of active compound, 1 part by weight of active compound is mixed with the stated amounts of solvents and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of *Sphaerotheca fuliginea*. The plants are then placed in a greenhouse at about 23° C. and a relative atmospheric humidity of about 70%.

Evaluation is carried out 7 days after the inoculation. 0% means an efficacy which corresponds to that of the control, whereas an efficacy of 100% means that no infection is observed.

Active compounds, application rates and test results are shown in the table below.

TABLE B

Sphaerotheca test (cucumber)/protective

| Active compound | Application rate of active compound in g/ha | Efficacy in % |
|---|---|---|
| 2 (structure) | 100 | 100 |
| 3 (structure) | 100 | 98 |

TABLE B-continued

Sphaerotheca test (cucumber)/protective

| Active compound | | Application rate of active compound in g/ha | Efficacy in % |
|---|---|---|---|
| 4 | [structure: 3-methylthiophene-2-carboxamide linked to phenyl-benzodioxole-CF2] | 100 | 100 |
| 5 | [structure: 4-CF3-2-methylthiazole-5-carboxamide linked to phenyl-benzodioxole-CF2] | 100 | 100 |
| 6 | [structure: 2-CF3-benzamide linked to phenyl-benzodioxin-CF2CF2] | 100 | 100 |
| 9 | [structure: 3-methylthiophene-2-carboxamide linked to phenyl-benzodioxin-CF2CF2] | 100 | 100 |
| 10 | [structure: 4-CF3-2-methylthiazole-5-carboxamide linked to phenyl-benzodioxin-CF2CF2] | 100 | 100 |
| 19 | [structure: 3-methyl-5-fluoro-1-methylpyrazole-4-carboxamide linked to phenyl-benzodioxole-CF2] | 100 | 92 |
| 1 | [structure: 3-methyl-5-fluoro-1-methylpyrazole-4-carboxamide linked to phenyl-benzodioxin-CF2CF2] | 100 | 98 |

Example C

*Venturia* Test (Apple)/Protective

Solvents:
   24.5 parts by weight of acetone
   24.5 parts by weight of dimethylacetamide Emulsifier:
   1.0 part by weight of alkylaryl polyglycol ether To produce a suitable preparation of active compound, 1 part by weight of active compound is mixed with the stated amounts of solvents and emulsifier, and the concentrate is diluted with water to the desired concentration.

To test for protective activity, young plants are sprayed with the preparation of active compound at the stated application rate. After the spray coating has dried on, the plants are inoculated with an aqueous conidia suspension of the apple scab pathogen *Venturia inaequalis* and then remain in an incubation cabin at about 20° C. in 100% relative atmospheric humidity for 1 day.

The plants are then placed in a greenhouse at about 21° C. and a relative atmospheric humidity of about 90%.

Evaluation is carried out 10 days after the inoculation. 0% means an efficacy which corresponds to that of the control, whereas an efficacy of 100% means that no infection is observed.

Active compounds, application rates and test results are shown in the table below.

TABLE C

Venturia test (apple)/protective

| Active compound | Application rate of active compound in g/ha | Efficacy in % |
|---|---|---|
| 2 | 100 | 100 |
| 4 | 100 | 98 |
| 5 | 100 | 100 |
| 6 | 100 | 99 |
| 10 | 100 | 100 |
| 19 | 100 | 96 |
| 1 | 100 | 100 |

Example D

Alternaria Test (Tomato)/Protective

Solvent:
  49 parts by weight of N,N-dimethylformamide

Emulsifier:
  1 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young tomato plants are sprayed with the preparation of active compound at the stated application rate. 1 day after the treatment, the plants are inoculated with a spore suspension of Alternaria solani and then remain at 100% relative humidity and at 20° C. for 24 h. The plants then remain at 96% relative atmospheric humidity and a temperature of 20° C.

Evaluation is carried out 7 days after the inoculation. 0% means an efficacy which corresponds to that of the control, whereas an efficacy of 100% means that no infection is observed.

Active compounds, application rates and test results are shown in the table below.

TABLE D

Alternaria test (tomato)/protective

| Active compound | Application rate of active compound in g/ha | Efficacy in % |
| --- | --- | --- |
| 2 | 750 | 100 |
| 3 | 750 | 94 |
| 9 | 750 | 95 |
| 15 | 750 | 95 |

Example E

Puccinia Test (Wheat)/Protective

Solvent:
  25 parts by weight of N,N-dimethylacetamide

Emulsifier:
  0.6 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are sprayed with a conidia suspension of *Puccinia recondita*. The plants remain in an incubation cabin at 20° C. and 100% relative atmospheric humidity for 48 hours.

The plants are then placed in a greenhouse at a temperature of about 20° C. and a relative atmospheric humidity of 80% to promote the development of rust pustules.

Evaluation is carried out 10 days after the inoculation. 0% means an efficacy which corresponds to that of the control, whereas an efficacy of 100% means that no infection is observed.

Active compounds, application rates and test results are shown in the table below.

TABLE E

Puccinia test (wheat)/protective

| Active compound | Application rate of active compound in g/ha | Efficacy in % |
|---|---|---|
| 1 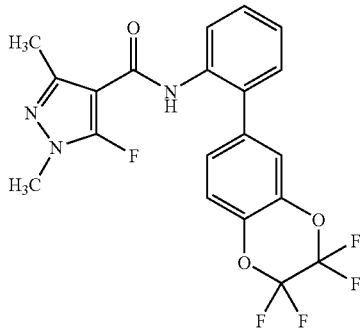 | 500 | 100 |

Example F

Inhibitory Test Using a Giant Colony of Basidiomycetes

Mycelium pieces were punched out of a giant colony of the Basidiomycetes species *Coriolus versicolor* and incubated at 26° C. on a nutrient agar medium containing malt extract peptone. The inhibition of the growth of the fungal threads on active-compound-containing nutrient media was compared to the longitudinal growth on nutrient media without added active compound and rated as inhibition in percent.

In this test, for example, the following compounds according to the invention of the Preparation Examples show good activity:

TABLE F

Inhibitory test using a giant colony of Basidiomycetes

| Active compound | Application rate of active compound in ppm | Inhibition ppm |
|---|---|---|
| 19 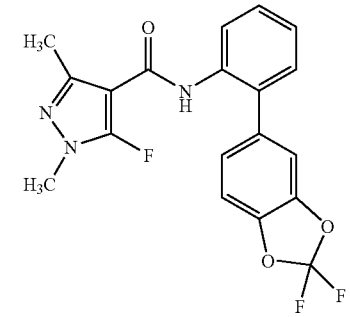 | 6 | 100 |

TABLE F-continued

Inhibitory test using a giant colony of Basidiomycetes

| Active compound | Application rate of active compound in ppm | Inhibition ppm |
|---|---|---|
| 1 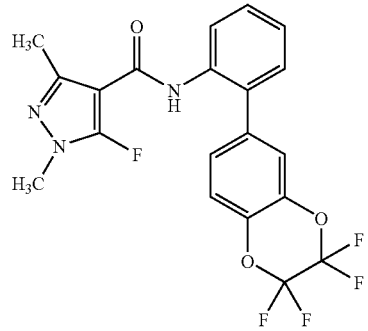 | 6 | 100 |

The invention claimed is:

1. A biphenylcarboxamide of the formula (I)

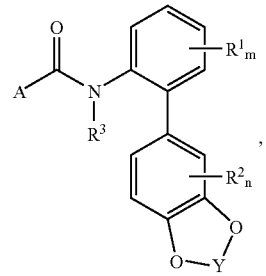

(I)

in which
$R^1$ and $R^2$ independently of one another represent hydrogen, halogen, cyano, nitro, $C_1$–$C_8$-alkyl, $C_1$–$C_8$-alkoxy, or $C_1$–$C_8$-alkylthio, or represent $C_1$–$C_6$-haloalkyl, $C_1$–$C_6$-haloalkoxy, or $C_1$–$C_6$-haloalkylthio having in each case 1 to 13 fluorine, chlorine and/or bromine atoms, m represents 1, 2, 3 or 4, with the proviso that $R^1$ represents identical or different radicals if m represents 2, 3 or 4, n represents 1, 2 or 3, with the proviso that $R^2$ represents identical or different radicals if n represents 2 or 3, $R^3$ represents hydrogen, hydroxyl, $C_1$–$C_6$-alkyl, $C_3$–$C_6$-cycloalkyl, $C_1$–$C_6$-alkoxy, $C_1$–$C_6$-alkoxy-$C_1$–$C_6$-alkyl, cyano-$C_1$–$C_6$-alkyl, $C_1$–$C_6$-haloalkyl having 1 to 7 halogen atoms, $C_1$–$C_6$-alkylamino, $C_1$–$C_6$-alkylsulphenyl, $C_1$–$C_6$-haloalkyl-sulphenyl having 1 to 7 halogen atoms, ($C_1$–$C_6$-alkyl)carbonyl, carbamoyl, Y represents carbonyl or represents $C_1$–$C_3$-alkylene which is optionally mono- or polysubstituted by identical or different substituents from the group consisting of halogen, $C_1$–$C_6$-alkyl, $C_1$–$C_6$-alkoxy, $C_1$–$C_6$-alkylthio, $C_1$–$C_6$-haloalkyl having 1 to 13 flourine, chlorine, and/or bromine atoms, $C_1$–$C_6$-haloalkoxy having 1 to 13 flourine, chlorine, and/or bromine atoms, and $C_1$–$C_6$-haloalkylthio having 1 to 13 flourine, chlorine, and/or bromine atoms, and A represents (1) a radical of the formula

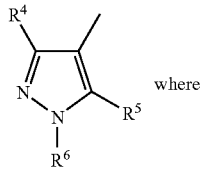

where

- $R^4$ represents hydrogen, cyano, halogen, nitro, $C_1$–$C_4$-alkyl, $C_1$–$C_4$-haloalkyl having 1 to 5 halogen atoms, $C_3$–$C_6$-cycloalkyl, $C_1$–$C_4$-alkoxy, $C_1$–$C_4$-haloalkoxy having 1 to 5 halogen atoms, $C_1$–$C_4$-alkylthio, $C_1$–$C_4$-haloalkylthio having 1 to 5 halogen atoms, aminocarbonyl or aminocarbonyl-$C_1$–$C_4$-alkyl,
- $R^5$ represents hydrogen, halogen, cyano, $C_1$–$C_4$-alkyl, $C_1$–$C_4$-alkoxy, or $C_1$–$C_4$-alkylthio, and
- $R^6$ represents hydrogen, $C_1$–$C_4$-alkyl, $C_1$–$C_4$-haloalkyl having 1 to 5 halogen atoms, hydroxy-$C_1$–$C_4$-alkyl, $C_2$–$C_6$-alkenyl, $C_3$–$C_6$-cycloalkyl, $C_1$–$C_4$-alkylthio-$C_1$–$C_4$-alkyl, $C_1$–$C_4$-haloalkylthio-$C_1$–$C_4$-alkyl having 1 to 5 halogen atoms, $C_1$–$C_4$-alkoxy-$C_1$–$C_4$-alkyl, $C_1$–$C_4$-haloalkoxy-$C_1$–$C_4$-alkyl having 1 to 5 halogen atoms or phenyl, or (2) a radical of the formula

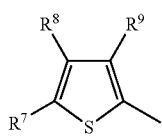

where

- $R^7$ and $R^8$ independently of one another represent hydrogen, halogen, $C_1$–$C_4$-alkyl, or $C_1$–$C_4$-haloalkyl having 1 to 5 halogen atoms, and
- $R^9$ represents halogen, cyano or $C_1$–$C_4$-alkyl or $C_1$–$C_4$-haloalkoxy having 1 to 5 halogen atoms, or (3) a radical of the formula

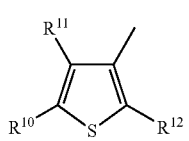

where

- $R^{10}$ and $R^{11}$ independently of one another represent hydrogen, halogen, $C_1$–$C_4$-alkyl, or $C_1$–$C_4$-haloalkyl having 1 to 5 halogen atoms, and
- $R^{12}$ represents hydrogen, $C_1$–$C_4$-alkyl or halogen, or (4) a radical of the formula

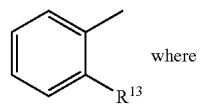

where

- $R^{13}$ represents hydrogen, halogen, hydroxyl, cyano, $C_1$–$C_6$-alkyl, $C_1$–$C_4$-haloalkyl having 1 to 5 halogen atoms, $C_1$–$C_4$-haloalkoxy having 1 to 5 halogen atoms, or $C_1$–$C_4$-haloalkylthio having 1 to 5 halogen atoms, or (5) a radical of the formula

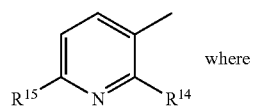

where

- $R^{14}$ represents halogen, hydroxyl, cyano, $C_1$–$C_4$-alkyl, $C_1$–$C_4$-haloalkyl having 1 to 5 halogen atoms, $C_1$–$C_4$-alkoxy, $C_1$–$C_4$-alkylthio, $C_1$–$C_4$-haloalkylthio having 1 to 5 halogen atoms, or $C_1$–$C_4$-haloalkoxy having 1 to 5 halogen atoms, and
- $R^{15}$ represents hydrogen, halogen, cyano, $C_1$–$C_4$-alkyl, $C_1$–$C_4$-haloalkyl having 1 to 5 halogen atoms, $C_1$–$C_4$-alkoxy, $C_1$–$C_4$-alkylthio, $C_1$–$C_4$-haloalkoxy having 1 to 5 halogen atoms, $C_1$–$C_4$-alkylsulphinyl, or $C_1$–$C_4$-alkylsulphonyl, or (6) a radical of the formula

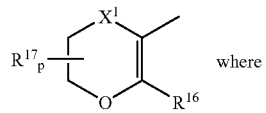

where

- $R^{16}$ represents $C_1$–$C_4$-alkyl or $C_1$–$C_4$-haloalkyl having 1 to 5 halogen atoms,
- $R^{17}$ represents $C_1$–$C_4$-alkyl,
- $X^1$ represents a sulphur atom, represents SO, $SO_2$, or $CH_2$, and
- p represents 0, 1 or 2, with the proviso that $R^{17}$ represents identical or different radicals if p represents 2, or (7) a radical of the formula

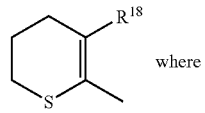

where

- $R^{18}$ represents $C_1$–$C_4$-alkyl or $C_1$–$C_4$-haloalkyl having 1 to 5 halogen atoms, or (8) a radical of the formula

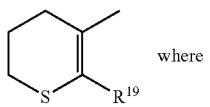 where

R$^{19}$ represents C$_1$–C$_4$-alkyl or C$_1$–C$_4$-haloalkyl having 1 to 5 halogen atoms, or (9) a radical of the formula

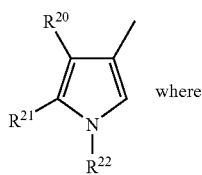 where

R$^{20}$ represents halogen, cyano, C$_1$–C$_4$-alkyl, or C$_1$–C$_4$-haloalkyl having 1 to 5 halogen atoms,
R$^{21}$ represents hydrogen, halogen, C$_1$–C$_4$-alkyl, or C$_1$–C$_4$-haloalkyl having 1 to 5 halogen atoms, and
R$^{22}$ represents hydrogen, cyano, C$_1$–C$_4$-alkyl, C$_1$–C$_4$-haloalkyl having 1 to 5 halogen atoms, C$_1$–C$_4$-alkoxy-C$_1$–C$_4$-alkyl, hydroxy-C$_1$–C$_4$-alkyl, C$_1$–C$_4$-alkylsulphonyl, di(C$_1$–C$_4$-alkyl)-aminosulphonyl, C$_1$–C$_6$-alkylcarbonyl or optionally substituted phenylsulphonyl or benzoyl, or

(10) a radical of the formula

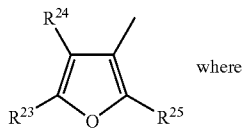 where

R$^{23}$ and R$^{24}$ independently of one another represent hydrogen, halogen, amino, C$_1$–C$_4$-alkyl, or C$_1$–C$_4$-haloalkyl having 1 to 5 halogen atoms, and
R$^{25}$ represents hydrogen, halogen, C$_1$–C$_4$-alkyl, or C$_1$–C$_4$-haloalkyl having 1 to 5 halogen atoms, or

(11) a radical of the formula

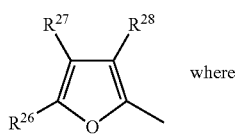 where

R$^{26}$ and R$^{27}$ independently of one another represent hydrogen, halogen, amino, nitro, C$_1$–C$_4$-alkyl, or C$_1$–C$_4$-haloalkyl having 1 to 5 halogen atoms, and
R$^{28}$ represents hydrogen, halogen, C$_1$–C$_4$-alkyl, or C$_1$–C$_4$-haloalkyl having 1 to 5 halogen atoms, or

(12) a radical of the formula

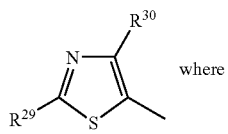 where

R$^{29}$ represents hydrogen, halogen, amino, C$_1$–C$_4$-alkylamino, di-(C$_1$–C$_4$-alkyl)amino, cyano, C$_1$–C$_4$-alkyl or C$_1$–C$_4$-haloalkyl having 1 to 5 halogen atoms, and
R$^{30}$ represents halogen, C$_1$–C$_4$-alkyl, or C$_1$–C$_4$-haloalkyl having 1 to 5 halogen atoms, or

(13) a radical of the formula

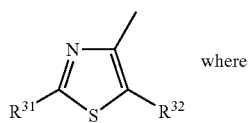 where

R$^{31}$ represents hydrogen, halogen, amino, C$_1$–C$_4$-alkylamino, di-(C$_1$–C$_4$-alkyl)amino, cyano, C$_1$–C$_4$-alkyl or C$_1$–C$_4$-haloalkyl having 1 to 5 halogen atoms, and
R$^{32}$ represents halogen, C$_1$–C$_4$-alkyl, or C$_1$–C$_4$-haloalkyl having 1 to 5 halogen atoms, or

(14) a radical of the formula

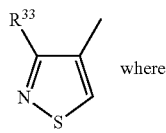 where

R$^{33}$ represents halogen, C$_1$–C$_4$-alkyl or C$_1$–C$_4$-haloalkyl having 1 to 5 halogen atoms,

(15) a radical of the formula

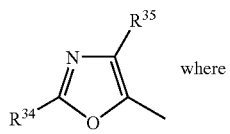 where

R$^{34}$ represents hydrogen or C$_1$–C$_4$-alkyl, and
R$^{35}$ represents halogen or C$_1$–C$_4$-alkyl, or

(16) a radical of the formula

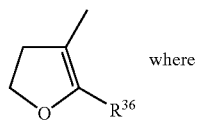 where $R^{36}$ represents $C_1$–$C_4$-alkyl or $C_1$–$C_4$-haloalkyl having 1 to 5 halogen atoms, or

(17) a radical of the formula

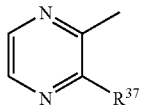 where $R^{37}$ represents hydrogen, halogen or $C_1$–$C_4$-alkyl.

2. A biphenylcarboxamide of the formula (I) according to claim 1 in which $R^1$ and $R^2$ independently of one another represent hydrogen, fluorine, chlorine, bromine, cyano, nitro, $C_1$–$C_6$-alkyl, $C_1$–$C_6$-alkoxy, $C_1$–$C_6$-alkylthio, or represent $C_1$–$C_4$-haloalkyl, $C_1$–$C_4$-haloalkoxy, or $C_1$–$C_4$-haloalkylthio having in each case 1 to 9 fluorine, chlorine and/or bromine atoms, m represents 1, 2 or 3, with the proviso that $R^1$ represents identical or different radicals if m represents 2 or 3, n represents 1, 2 or 3, with the proviso that $R^2$ represents identical or different radicals if n represents 2 or 3, $R^3$ represents hydrogen, hydroxyl, $C_1$–$C_4$-alkyl, $C_3$–$C_6$-cycloalkyl, $C_1$–$C_4$-alkoxy, $C_1$–$C_3$-alkoxy-$C_1$–$C_2$-alkyl, cyano-$C_1$–$C_4$-alkyl, $C_1$–$C_4$-haloalkyl having 1 to 5 halogen atoms, $C_1$–$C_4$-aminoalkyl, $C_1$–$C_4$-alkylsulphenyl, $C_1$–$C_4$-haloalkyl-sulphenyl having 1 to 5 halogen atoms, or ($C_1$–$C_4$-alkyl)carbonyl, Y represents carbonyl or represents $C_1$–$C_2$-alkylene that is optionally mono- or polysubstituted by identical or different substituents selected from the group consisting of fluorine, chlorine, bromine, $C_1$–$C_4$-alkyl, $C_1$–$C_4$-alkoxy, $C_1$–$C_4$-alkylthio, $C_1$–$C_4$-haloalkyl having 1 to 9 flourine, chlorine, and/or bromine atoms, $C_1$–$C_4$-haloalkoxy having 1 to 9 flourine, chlorine, and/or bromine atoms, and $C_1$–$C_4$-haloalkylthio having 1 to 9 fluorine, chlorine, and/or bromine atoms, and A represents (1) a radical of the formula

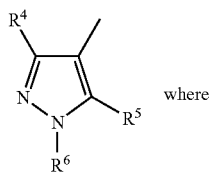 where $R^4$ represents hydrogen, cyano, fluorine, chlorine, bromine, iodine, methyl, ethyl, i-propyl, $C_1$–$C_2$-haloalkyl having 1 to 5 fluorine, chlorine and/or bromine atoms, cyclopropyl, methoxy, ethoxy, $C_1$–$C_2$-haloalkoxy having 1 to 5 fluorine and/or bromine atoms, methylthio, ethylthio, trifluoromethylthio, difluoromethylthio, aminocarbonyl, aminocarbonylmethyl, or aminocarbonylethyl, $R^5$ represents hydrogen, fluorine, chlorine, bromine, iodine, methyl, ethyl, methoxy, ethoxy, methylthio, or ethylthio, and $R^6$ represents hydrogen, methyl, ethyl, n-propyl, i-propyl, $C_1$–$C_2$-haloalkyl having 1 to 5 fluorine, chlorine and/or bromine atoms, hydroxymethyl, hydroxyethyl, cyclopropyl, cyclopentyl, cyclohexyl or phenyl, or (2) a radical of the formula

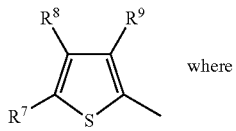 where $R^7$ and $R^8$ independently of one another represent hydrogen, fluorine, chlorine, bromine, methyl, ethyl or $C_1$–$C_2$-haloalkyl having 1 to 5 fluorine, chlorine, and/or bromine atoms, and $R^9$ represents fluorine, chlorine, bromine, cyano, methyl, ethyl, or $C_1$–$C_2$-haloalkoxy having 1 to 5 fluorine, chlorine, and/or bromine atoms, or (3) a radical of the formula

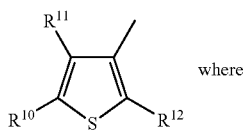 where $R^{10}$ and $R^{11}$ independently of one another represent hydrogen, fluorine, chlorine, bromine, methyl, ethyl, or $C_1$–$C_2$-haloalkyl having 1 to 5 fluorine, chlorine, and/or bromine atoms, and $R^{12}$ represents hydrogen, fluorine, chlorine, bromine, methyl, or ethyl, or (4) a radical of the formula

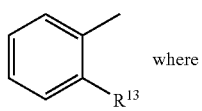 where $R^{13}$ represents hydrogen, fluorine, chlorine, bromine, iodine, hydroxyl, cyano, $C_1$–$C_4$-alkyl, $C_1$–$C_2$-haloalkyl having 1 to 5 fluorine, chlorine and/or bromine atoms, $C_1$–$C_2$-haloalkoxy having 1 to 5 fluorine, chlorine and/or bromine atoms, or $C_1$–$C_2$-haloalkylthio having 1 to 5 fluorine, chlorine, and/or bromine atoms, or (5) a radical of the formula

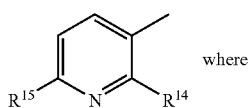 where $R^{14}$ represents fluorine, chlorine, bromine, iodine, hydroxyl, cyano, $C_1$–$C_4$-alkyl, $C_1$–$C_2$-haloalkyl having 1 to 5 fluorine, chlorine and/or bromine atoms, methoxy, ethoxy, methylthio, ethylthio, difluoromethylthio, trifluoromethylthio, or $C_1$–$C_2$-haloalkoxy having 1 to 5 fluorine, chlorine and/or bromine atoms, and $R^{15}$ represents hydrogen, fluorine, chlorine, bromine, iodine, cyano, $C_1$–$C_4$-alkyl, $C_1$–$C_2$-haloalkyl having 1 to 5 fluorine, chlorine, and/or bromine atoms, methoxy, ethoxy, methylthio, ethylthio, $C_1$–$C_2$-haloalkoxy having 1 to 5 fluorine, chlorine, and/or bromine atoms, $C_1$–$C_2$-alkylsulphinyl, or $C_1$–$C_2$-alkylsulphonyl, or (6) a radical of the formula

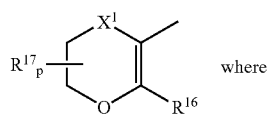  where $R^{16}$ represents methyl, ethyl or $C_1$–$C_2$-haloalkyl having 1 to 5 fluorine, chlorine and/or bromine atoms, $R^{17}$ represents methyl or ethyl, $X^1$ represents a sulphur atom, represents SO, $SO_2$, or $CH_2$, and p represents 0, 1 or 2, with the proviso that $R^{17}$ represents identical or different radicals if p represents 2, or (7) a radical of the formula

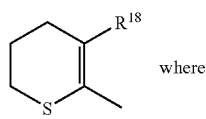  where $R^{18}$ represents methyl, ethyl or $C_1$–$C_2$-haloalkyl having 1 to 5 fluorine, chlorine and/or bromine atoms, or (8) a radical of the formula

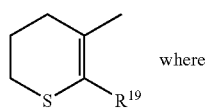  where $R^{19}$ represents methyl, ethyl or $C_1$–$C_2$-haloalkyl having 1 to 5 fluorine, chlorine, and/or bromine atoms, or (9) a radical of the formula

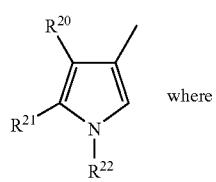  where $R^{20}$ represents fluorine, chlorine, bromine, cyano, methyl, ethyl, i-propyl, or $C_1$–$C_2$-haloalkyl having 1 to 5 fluorine, chlorine, and/or bromine atoms, $R^{21}$ represents hydrogen, fluorine, chlorine, bromine, methyl, ethyl or $C_1$–$C_2$-haloalkyl having 1 to 5 fluorine, chlorine, and/or bromine atoms, and $R^{22}$ represents hydrogen, methyl, ethyl, $C_1$–$C_2$-haloalkyl having 1 to 5 fluorine, chlorine, and/or bromine atoms, $C_1$–$C_2$-alkoxy-$C_1$–$C_2$-alkyl, hydroxymethyl, hydroxyethyl, methylsulphonyl, or dimethylaminosulphonyl, or

(10) a radical of the formula

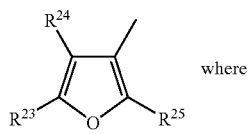  where $R^{23}$ and $R^{24}$ independently of one another represent hydrogen, fluorine, chlorine, bromine, amino, methyl, ethyl, or $C_1$–$C_2$-haloalkyl having 1 to 5 fluorine, chlorine, and/or bromine atoms, and $R^{25}$ represents hydrogen, fluorine, chlorine, bromine, methyl, ethyl, or $C_1$–$C_2$-haloalkyl having 1 to 5 fluorine, chlorine, and/or bromine atoms, or

(11) a radical of the formula

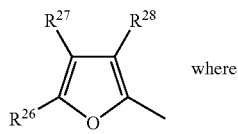  where $R^{26}$ and $R^{27}$ independently of one another represent hydrogen, fluorine, chlorine, bromine, amino, nitro, methyl, ethyl, or $C_1$–$C_2$-haloalkyl having 1 to 5 fluorine, chlorine, and/or bromine atoms, and $R^{28}$ represents hydrogen, fluorine, chlorine, bromine, methyl, ethyl, or $C_1$–$C_2$-haloalkyl having 1 to 5 fluorine, chlorine, and/or bromine atoms, or

(12) a radical of the formula

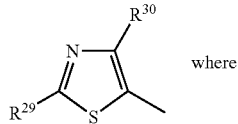  where $R^{29}$ represents hydrogen, fluorine, chlorine, bromine, amino, $C_1$–$C_4$-alkylamino, di($C_1$–$C_4$-alkyl)amino, cyano, methyl, ethyl, or $C_1$–$C_2$-haloalkyl having 1 to 5 fluorine, chlorine, and/or bromine atoms and $R^{30}$ represents fluorine, chlorine, bromine, methyl, ethyl, or $C_1$–$C_2$-haloalkyl having 1 to 5 fluorine, chlorine and/or bromine atoms, or

(13) a radical of the formula

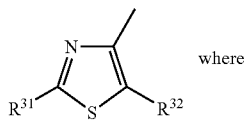

where

R³¹ represents hydrogen, fluorine, chlorine, bromine, amino, $C_1$–$C_4$-alkylamino, di($C_1$–$C_4$-alkyl)amino, cyano, methyl, ethyl, or $C_1$–$C_2$-haloalkyl having 1 to 5 fluorine, chlorine, and/or bromine atoms, and R³² represents fluorine, chlorine, bromine, methyl, ethyl, or $C_1$–$C_2$-haloalkyl having 1 to 5 fluorine, chlorine and/or bromine atoms, or

(14) a radical of the formula

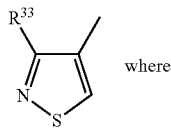

where

R³³ represents fluorine, chlorine, bromine, methyl, ethyl or $C_1$–$C_2$-haloalkyl having 1 to 5 fluorine, chlorine and/or bromine atoms, or

(15) a radical of the formula

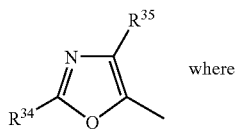

where

R³⁴ represents hydrogen, methyl, or ethyl, and
R³⁵ represents fluorine, chlorine, bromine, methyl, or ethyl, or

(16) a radical of the formula

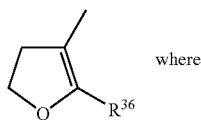

where

R³⁶ represents methyl, ethyl, or $C_1$–$C_2$-haloalkyl having 1 to 5 fluorine, chlorine and/or bromine atoms, or

(17) a radical of the formula

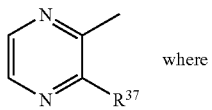

where

R³⁷ represents hydrogen, fluorine, chlorine, bromine, methyl, or ethyl.

3. A biphenylcarboxamide of the formula (I) according to claim 1 in which

R¹ and R² independently of one another represent hydrogen, fluorine, chlorine, bromine, cyano, nitro, methyl, ethyl, n-propyl, i-propyl, n-butyl, i-butyl, s-butyl, t-butyl, methoxy, ethoxy, methylthio, ethylthio, trichloromethyl, trifluoromethyl, difluoromethyl, difluorochloromethyl, difluoromethoxy, trifluoromethoxy, trifluoromethylthio, difluorochloromethylthio, m represents 1 or 2, with the proviso that R¹ represents identical or different radicals if m represents 2, n represents 1 or 2, with the proviso that R² represents identical or different radicals if n represents 2, R³ represents hydrogen, hydroxyl, methyl, ethyl, n-propyl, i-propyl, n-, i-, s-, or t-butyl, cyclopropyl, cyclobutyl, cyclopentyl, cyclohexyl, methoxy, ethoxy, methoxymethyl, cyanomethyl, difluoromethyl, methylsulphenyl, trichloromethylsulphenyl or acetyl, Y represents carbonyl or represents —CH₂— or —(CH₂)₂— that are each optionally mono- to tetrasubstituted by identical or different substituents selected from the group consisting of fluorine, chlorine, bromine, methyl, ethyl, i-propyl, t-butyl, methoxy, i-propoxy, t-butoxy, methylthio, i-propylthio, t-butylthio, trifluoromethyl, trifluoromethoxy, and trifluoromethylthio, and A represents (1) a radical of the formula

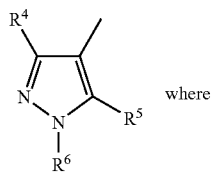

where

R⁴ represents hydrogen, fluorine, chlorine, bromine, iodine, methyl, ethyl, i-propyl, monofluoromethyl, difluoromethyl, trifluoromethyl, difluorochloromethyl, trichloromethyl, cyclopropyl, methoxy, ethoxy, trifluoromethoxy, trichloromethoxy, methylthio, ethylthio, trifluoromethylthio or difluoromethylthio R⁵ represents hydrogen, fluorine, chlorine, bromine, iodine, methyl, ethyl, methoxy, ethoxy, methylthio, or ethylthio, and R⁶ represents hydrogen, methyl, ethyl, trifluoromethyl, difluoromethyl, hydroxymethyl, hydroxyethyl or phenyl, or (2) a radical of the formula

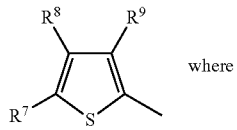

where

R⁷ and R⁸ independently of one another represent hydrogen, fluorine, chlorine, bromine, methyl, ethyl, difluoromethyl, trifluoromethyl, difluorochloromethyl, or trichloromethyl, and $R^9$ represents fluorine, chlorine, bromine, cyano, methyl, trifluoromethoxy, difluoromethoxy, difluorochloromethoxy, or trichloromethoxy, or (3) a radical of the formula

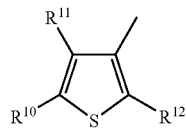 where $R^{10}$ and $R^{11}$ independently of one another represent hydrogen, fluorine, chlorine, bromine, methyl, ethyl, difluoromethyl, trifluoromethyl, difluorochloromethyl, or trichloromethyl, and $R^{12}$ represents hydrogen, fluorine, chlorine, bromine, methyl, or ethyl, or (4) a radical of the formula

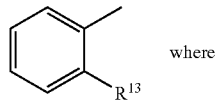 where $R^{13}$ represents hydrogen, fluorine, chlorine, bromine, iodine, hydroxyl, cyano, methyl, ethyl, n-propyl, i-propyl, n-butyl, i-butyl, s-butyl, t-butyl, difluoromethyl, trifluoromethyl, difluorochloromethyl, trichloromethyl, trifluoromethoxy, difluoromethoxy, difluorochloromethoxy, trichloromethoxy, trifluoromethylthio, difluoromethylthio, difluorochloromethylthio, or trichloromethylthio, or (5) a radical of the formula

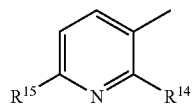 where $R^{14}$ represents fluorine, chlorine, bromine, iodine, hydroxyl, cyano, methyl, ethyl, n-propyl, i-propyl, n-butyl, i-butyl, s-butyl, t-butyl, trifluoromethyl, difluoromethyl, difluorochloromethyl, trichloromethyl, methoxy, ethoxy, methylthio, ethylthio, difluoromethylthio, trifluoromethylthio, trifluoromethoxy, difluoromethoxy, difluorochloromethoxy, or trichloromethoxy, and $R^{15}$ represents hydrogen, fluorine, chlorine, bromine, iodine, cyano, n-propyl, i-propyl, n-butyl, i-butyl, s-butyl, t-butyl, trifluoromethyl, difluoromethyl, difluorochloromethyl, trichloromethyl, methoxy, ethoxy, methylthio, ethylthio, trifluoromethoxy, difluoromethoxy, difluorochloromethoxy, trichloromethoxy, methylsulphinyl, or methylsulphonyl, or (6) a radical of the formula

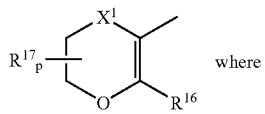 where $R^{16}$ represents methyl, ethyl, trifluoromethyl, difluoromethyl, difluorochloromethyl, or trichloromethyl, $R^{17}$ represents methyl or ethyl, $X^1$ represents a sulphur atom or represents SO, $SO_2$, or $CH_2$, and p represents 0, 1 or 2, with the proviso that $R^{17}$ represents identical or different radicals if p represents 2, or (7) a radical of the formula

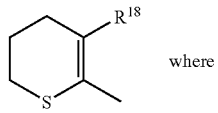 where $R^{18}$ represents methyl, ethyl, trifluoromethyl, difluoromethyl, difluorochloromethyl, or trichloromethyl, or (8) a radical of the formula

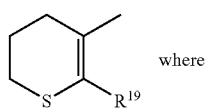 where $R^{19}$ represents methyl, ethyl, trifluoromethyl, difluoromethyl, difluorochloromethyl, or trichloromethyl, or (9) a radical of the formula

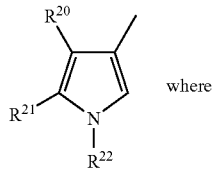 where $R^{20}$ represents fluorine, chlorine, bromine, cyano, methyl, ethyl, i-propyl, trifluoromethyl, difluoromethyl, difluorochloromethyl, or trichloromethyl, $R^{21}$ represents hydrogen, fluorine, chlorine, bromine, methyl, ethyl, trifluoromethyl, difluoromethyl, or trichloromethyl, and $R^{22}$ represents hydrogen, methyl, ethyl, trifluoromethyl, methoxymethyl, ethoxymethyl, hydroxymethyl, or hydroxyethyl, or

(10) a radical of the formula

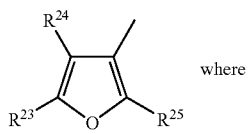 where

R²³ and R²⁴ independently of one another represent hydrogen, fluorine, chlorine, bromine, methyl, ethyl, trifluoromethyl, difluoromethyl, difluorochloromethyl, or trichloromethyl, and R²⁵ represents hydrogen, fluorine, chlorine, bromine, methyl, ethyl, trifluoromethyl, difluoromethyl, difluorochloromethyl, or trichloromethyl, or

(11) a radical of the formula

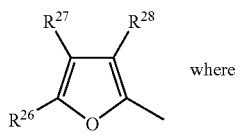 where

R²⁶ and R²⁷ independently of one another represent hydrogen, fluorine, chlorine, bromine, nitro, methyl, ethyl, trifluoromethyl, difluoromethyl, difluorochloromethyl, or trichloromethyl, and R²⁸ represents hydrogen, fluorine, chlorine, bromine, methyl, ethyl, trifluoromethyl, difluoromethyl, difluorochloromethyl, or trichloromethyl, or

(12) a radical of the formula

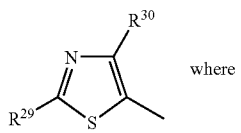 where

R²⁹ represents hydrogen, fluorine, chlorine, bromine, amino, methylamino, dimethylamino, cyano, methyl, ethyl, trifluoromethyl, difluoromethyl, difluorochloromethyl, or trichloromethyl, and R³⁰ represents fluorine, chlorine, bromine, methyl, ethyl, trifluoromethyl, difluoromethyl, difluorochloromethyl, or trichloromethyl, or

(13) a radical of the formula

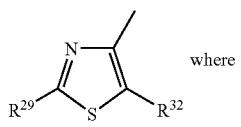 where

R³¹ represents hydrogen, fluorine, chlorine, bromine, amino, methylamino, dimethylamino, cyano, methyl, ethyl, trifluoromethyl, difluoromethyl, difluorochloromethyl, or trichloromethyl, and R³² represents fluorine, chlorine, bromine, methyl, ethyl, trifluoromethyl, difluoromethyl, difluorochloromethyl, or trichloromethyl, or

(14) a radical of the formula

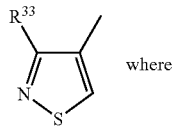 where

R³³ represents fluorine, chlorine, bromine, methyl, ethyl, trifluoromethyl, difluoromethyl, difluorochloromethyl, or trichloromethyl, or

(15) a radical of the formula

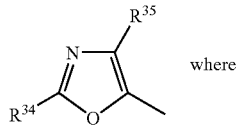 where

R³⁴ represents hydrogen, methyl, or ethyl, and

R³⁵ represents fluorine, chlorine, bromine, methyl, or ethyl, or

(16) a radical of the formula

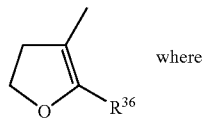 where

R³⁶ represents methyl, ethyl, trifluoromethyl, difluoromethyl, difluorochloromethyl, or trichloromethyl, or

(17) a radical of the formula

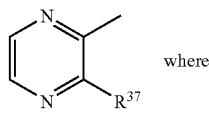 where

R³⁷ represents hydrogen, fluorine, chlorine, bromine, methyl, or ethyl.

4. A biphenylcarboxamide of the formula (I) according to claim 1 in which

R¹ and R² independently of one another represent hydrogen, fluorine, chlorine, bromine, methyl, ethyl, n-propyl, i-propyl, n-butyl, i-butyl, s-butyl, t-butyl, methoxy, ethoxy, methylthio, ethylthio, trichloromethyl, trifluoromethyl, difluoromethyl, trifluoromethoxy, trifluoromethylthio, m represents 1 or 2, with the proviso that R¹ represents identical or different radicals if m represents 2, n represents 1, $R^3$ represents hydrogen, methyl, ethyl, n-propyl, i-propyl, n-, i-, s-, or t-butyl, cyclopropyl, cyclopentyl or cyclohexyl, Y represents carbonyl or represents —CH$_2$— or —(CH$_2$)$_2$— that are each optionally mono- to tetrasubstituted by identical or different substituents from the group consisting of fluorine, methyl, i-propyl, t-butyl, methoxy, i-propoxy, t-butoxy, methylthio, i-propylthio, t-butylthio, trifluoromethyl, trifluoromethoxy, and trifluoromethylthio, and A represents (1) a radical of the formula

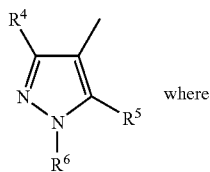

where $R^4$ represents hydrogen, fluorine, chlorine, bromine, iodine, methyl, i-propyl, monofluoromethyl, difluoromethyl, trifluoromethyl, difluorochloromethyl, or trichloromethyl, $R^5$ represents hydrogen, fluorine, chlorine, bromine, iodine, or methyl, and $R^6$ represents hydrogen, methyl, trifluoromethyl, or phenyl, or (2) a radical of the formula

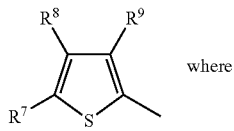

where $R^7$ and $R^8$ independently of one another represent hydrogen, fluorine, chlorine, bromine, methyl, ethyl, difluoromethyl, trifluoromethyl, or trichloromethyl, and $R^9$ represents fluorine, chlorine, bromine, methyl or trifluoromethoxy, or (3) a radical of the formula

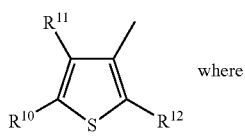

where $R^{10}$ and $R^{11}$ independently of one another represent hydrogen, fluorine, chlorine, bromine, methyl, ethyl, difluoromethyl, trifluoromethyl, or trichloromethyl, and $R^{12}$ represents hydrogen, fluorine, chlorine, bromine or methyl, or (4) a radical of the formula

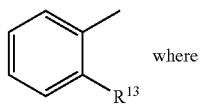

where $R^{13}$ represents hydrogen, fluorine, chlorine, bromine, iodine, methyl, difluoromethyl, trifluoromethyl, or trichloromethyl, or (5) a radical of the formula

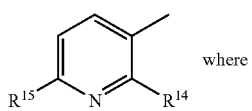

where $R^{14}$ represents fluorine, chlorine, bromine, iodine, methyl, trifluoromethyl, difluoromethyl, or trichloromethyl, and $R^{15}$ represents hydrogen, fluorine, chlorine, bromine, iodine, n-propyl, i-propyl, n-butyl, i-butyl, s-butyl, t-butyl, trifluoromethyl, difluoromethyl, trichloromethyl, methylsulphinyl, or methylsulphonyl, or (6) a radical of the formula

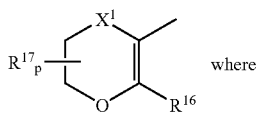

where $R^{16}$ represents methyl, ethyl, trifluoromethyl, difluoromethyl, or trichloromethyl, $R^{17}$ represents methyl or ethyl, $X^1$ represents a sulphur atom or represents SO, SO$_2$, or CH$_2$, and p represents 0, 1 or 2, with the proviso that $R^{17}$ represents identical or different radicals if p represents 2, or (7) a radical of the formula

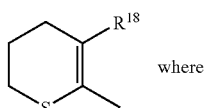

where $R^{18}$ represents methyl, trifluoromethyl, difluoromethyl, or trichloromethyl, or (8) a radical of the formula

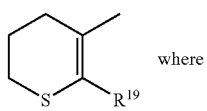

where $R^{19}$ represents methyl, trifluoromethyl, difluoromethyl, or trichloromethyl, or (9) a radical of the formula

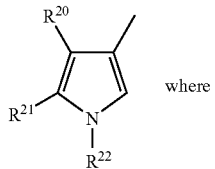 where $R^{20}$ represents fluorine, chlorine, bromine, methyl, i-propyl, trifluoromethyl, difluoromethyl, or trichloromethyl,
$R^{21}$ represents hydrogen, fluorine, chlorine, bromine, methyl, ethyl, trifluoromethyl, difluoromethyl, or trichloromethyl, and
$R^{22}$ represents hydrogen, methyl, ethyl, trifluoromethyl, or methoxymethyl, or

(10) a radical of the formula

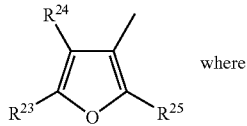 where $R^{23}$ and $R^{24}$ independently of one another represent hydrogen, fluorine, chlorine, bromine, methyl, trifluoromethyl, difluoromethyl, or trichloromethyl, and
$R^{25}$ represents hydrogen, fluorine, chlorine, bromine, methyl, trifluoromethyl, difluoromethyl, or trichloromethyl, or

(11) a radical of the formula

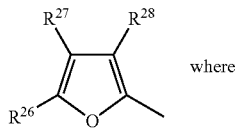 where $R^{26}$ and $R^{27}$ independently of one another represent hydrogen, fluorine, chlorine, bromine, methyl, trifluoromethyl, difluoromethyl, or trichloromethyl, and
$R^{28}$ represents hydrogen, fluorine, chlorine, bromine, methyl, trifluoromethyl, difluoromethyl, or trichloromethyl, or

(12) a radical of the formula

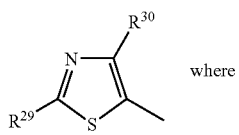 where $R^{29}$ represents hydrogen, fluorine, chlorine, bromine, amino, methylamino, dimethylamino, methyl, trifluoromethyl, difluoromethyl, or trichloromethyl, and
$R^{30}$ represents fluorine, chlorine, bromine, methyl, trifluoromethyl, difluoromethyl, or trichloromethyl, or

(13) a radical of the formula

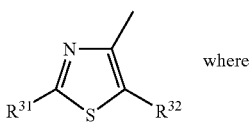 where $R^{31}$ represents hydrogen, fluorine, chlorine, bromine, amino, methylamino, dimethylamino, methyl, trifluoromethyl, difluoromethyl, or trichloromethyl, and
$R^{32}$ represents fluorine, chlorine, bromine, methyl, trifluoromethyl, difluoromethyl, or trichloromethyl, or

(14) a radical of the formula

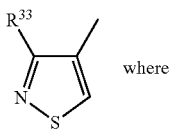 where $R^{33}$ represents fluorine, chlorine, bromine, methyl, trifluoromethyl, difluoromethyl, or trichloromethyl, or

(15) a radical of the formula

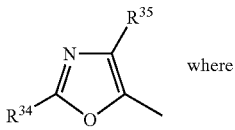 where $R^{34}$ represents hydrogen, methyl, or ethyl, and
$R^{35}$ represents fluorine, chlorine, bromine, methyl, or ethyl, or

(16) a radical of the formula

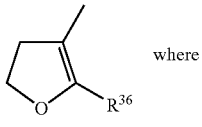 where $R^{36}$ represents methyl, trifluoromethyl, difluoromethyl, or trichloromethyl, or

(17) a radical of the formula

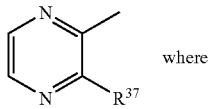
where $R^{37}$ represents hydrogen, fluorine, chlorine, bromine, or methyl.

5. A biphenylcarboxamide of the formula (I) according to claim 1 in which $R^1$ represents hydrogen, fluorine, chlorine, methyl,
$R^2$ represents hydrogen,
m represents 1 or 2, with the proviso that $R^1$ represents identical or different radicals if m represents 2,
n represents 1,
$R^3$ represents hydrogen,
Y represents —$CH_2$—, —$(CH_2)_2$—, —$CF_2$—, or —$(CF_2)_2$—, and
A represents (1) a radical of the formula

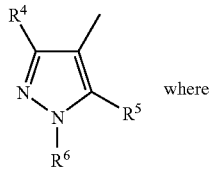
where $R^4$ represents methyl, monofluoromethyl, difluoromethyl, or trifluoromethyl, and
$R^5$ represents hydrogen, fluorine, chlorine, or methyl, and
$R^6$ represents methyl, or (2) a radical of the formula

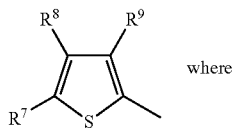
where $R^7$ and $R^8$ represent hydrogen, and
$R^9$ represents methyl, or (3) a radical of the formula

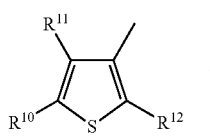
where $R^{10}$ and $R^{11}$ represent hydrogen, and
$R^{12}$ represents methyl, or (4) a radical of the formula

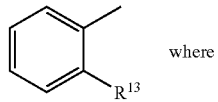
where $R^{13}$ represents iodine, methyl, difluoromethyl, or trifluoromethyl, or (5) a radical of the formula

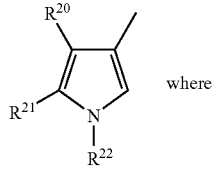
where $R^{20}$ represents methyl, trifluoromethyl, or difluoromethyl,
$R^{21}$ represents hydrogen, fluorine, chlorine, methyl, trifluoromethyl, or difluoromethyl, and
$R^{22}$ represents hydrogen, methyl, ethyl, trifluoromethyl, or methoxymethyl, or (6) a radical of the formula

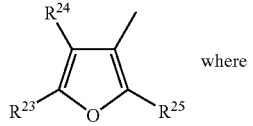
where $R^{23}$ and $R^{24}$ represent hydrogen, and
$R^{25}$ represents methyl, or (7) a radical of the formula

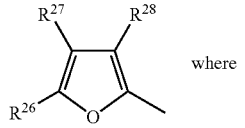
where $R^{26}$ and $R^{27}$ represent hydrogen, and
$R^{28}$ represents methyl, or (8) a radical of the formula

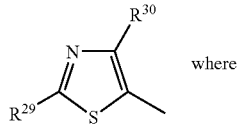
where $R^{29}$ represents amino, methylamino, dimethylamino, methyl, or trifluoromethyl, and
$R^{30}$ represents methyl, trifluoromethyl, or difluoromethyl, or (9) a radical of the formula

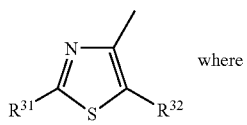 where $R^{31}$ represents amino, methylamino, dimethylamino, methyl, or trifluoromethyl, and $R^{32}$ represents methyl, trifluoromethyl, or difluoromethyl, or

(10) a radical of the formula

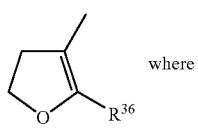 where $R^{36}$ represents methyl or trifluoromethyl.

6. A process for preparing biphenylcarboxamide of formula (I) according to claim 1 comprising a) reacting a carboxylic acid derivatives of formula (II)

 (II)

in which

A is as defined for formula (I) in claim 1, and

G represents halogen, hydroxyl or $C_1$–$C_6$-alkoxy, with an aniline derivative of formula (III)

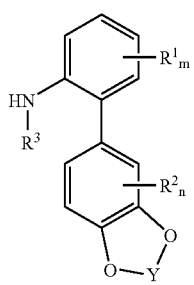 (III)

in which $R^1$, $R^2$, m, n, $R^3$ and Y are as defined for formula (I) in claim 1, optionally in the presence of a catalyst, optionally in the presence of an acid binder, and optionally in the presence of a diluent, or b) reacting a carboxamide derivative of formula (IV)

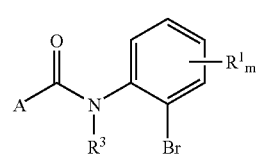 (IV)

in which $R^1$, m, $R^3$ and A are as defined for formula (I) in claim 1, with a boronic acid derivative of formula (V)

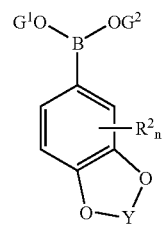 (V)

in which $R^2$, n and Y are as defined for formula (I) in claim 1, and $G^1$ and $G^2$ each represent hydrogen or together represent tetramethylethylene, in the presence of a catalyst, optionally in the presence of an acid binder, and optionally in the presence of a diluent, or c) reacting a carboxamide boronic acid derivative of formula (VI)

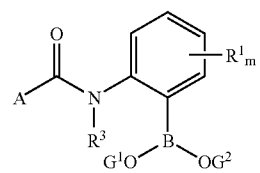 (VI)

in which $R^1$, m, $R^3$ and A are as defined for formula (I) in claim 1, and $G^1$ and $G^2$ each represent hydrogen or together represent tetramethylethylene, with phenyl derivative of formula (VII)

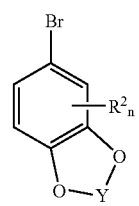 (VII)

in which $R^2$, n and Y are as defined for formula (I) in claim 1, in the presence of a catalyst, optionally in the presence of an acid binder, and optionally in the presence of a diluent, or d) reacting a carboxamide derivative of formula (IV)

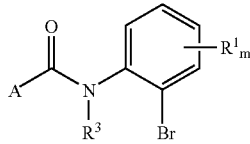

(IV)

in which $R^1$, m, $R^3$ and A are as defined for formula (I) in claim 1, with phenyl derivative of formula (VII)

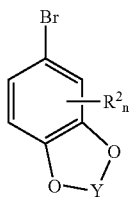

(VII)

in which $R^2$, n and Y are as defined for formula (I) in claim 1, in the presence of a palladium or platinum catalyst, in the presence of 4,4,4',4',5,5,5',5'-octamethyl-2,2'-bis-1,3,2-dioxaborolane, optionally in the presence of an acid binder, and optionally in the presence of a diluent.

7. A composition for controlling unwanted microorganisms comprising one or more biphenylcarboxamides of formula (I) according to claim 1 and one or more extenders and/or surfactants.

8. A process for preparing compositions for controlling unwanted microorganisms comprising mixing one or more biphenylcarboxamides of formula (I) according to claim 1 with one or more extenders and/or surfactants.

9. A method for controlling unwanted microorganisms comprising applying to the microorganisms and/or their habitats an effective amount of one or more biphenylcarboxamides of formula (I)

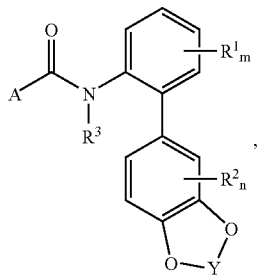

(I)

in which
$R^1$, $R^2$, and $R^3$ represent hydrogen,
m and n represent 1,

Y represents $C_1$–$C_3$-alkylene that is mono- or polysubstituted by fluorine, and A represents (1) a radical of the formula

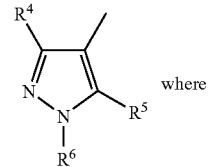

where $R^4$ represents hydrogen, cyano, halogen, nitro, $C_1$–$C_4$-alkyl, $C_1$–$C_4$-haloalkyl having 1 to 5 halogen atoms, $C_3$–$C_6$-cycloalkyl, $C_1$–$C_4$-alkoxy, $C_1$–$C_4$-haloalkoxy having 1 to 5 halogen atoms, $C_1$–$C_4$-alkylthio, $C_1$–$C_4$-haloalkylthio having 1 to 5 halogen atoms, aminocarbonyl, or aminocarbonyl-$C_1$–$C_4$-alkyl, $R^5$ represents hydrogen, halogen, cyano, $C_1$–$C_4$-alkyl, $C_1$–$C_4$-alkoxy, or $C_1$–$C_4$-alkylthio, and $R^6$ represents hydrogen, $C_1$–$C_4$-alkyl, $C_1$–$C_4$-haloalkyl having 1 to 5 halogen atoms, hydroxy-$C_1$–$C_4$-alkyl, $C_2$–$C_6$-alkenyl, $C_3$–$C_6$-cycloalkyl, $C_1$–$C_4$-alkylthio-$C_1$–$C_4$-alkyl, $C_1$–$C_4$-haloalkylthio-$C_1$–$C_4$-alkyl having 1 to 5 halogen atoms, $C_1$–$C_4$-alkoxy-$C_1$–$C_4$-alkyl, $C_1$–$C_4$-haloalkoxy-$C_1$–$C_4$-alkyl having 1 to 5 halogen atoms, or phenyl, or (2) a radical of the formula

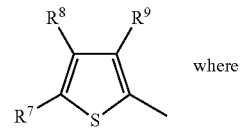

where $R^7$ and $R^8$ independently of one another represent hydrogen, halogen, $C_1$–$C_4$-alkyl, or $C_1$–$C_4$-haloalkyl having 1 to 5 halogen atoms, and $R^9$ represents halogen, cyano or $C_1$–$C_4$-alkyl, or $C_1$–$C_4$-haloalkoxy having 1 to 5 halogen atoms, or (3) a radical of the formula

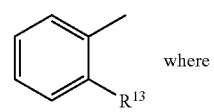

where where $R^{13}$ represents hydrogen, halogen, hydroxyl, cyano, $C_1$–$C_6$-alkyl, $C_1$–$C_4$-haloalkyl having 1 to 5 halogen atoms, $C_1$–$C_4$-haloalkoxy having 1 to 5 halogen atoms, or $C_1$–$C_4$-haloalkylthio having 1 to 5 halogen atoms, or (4) a radical of the formula
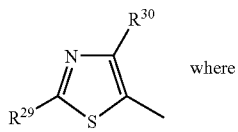 where
R$^{29}$ represents hydrogen, halogen, amino, $C_1$–$C_{04}$-alkylamino, di($C_1$–$C_4$-alkyl)amino, cyano, $C_1$–$C_4$-alkyl, or $C_1$–$C_4$-haloalkyl having 1 to 5 halogen atoms, and
R$^{30}$ represents halogen, $C_1$–$C_4$-alkyl, or $C_1$–$C_4$-haloalkyl having 1 to 5 halogen atoms.
* * * * *

UNITED STATES PATENT AND TRADEMARK OFFICE
CERTIFICATE OF CORRECTION

PATENT NO. : 7,208,169 B2  Page 1 of 1
APPLICATION NO. : 10/512706
DATED : April 24, 2007
INVENTOR(S) : Ralf Dunkel et al.

It is certified that error appears in the above-identified patent and that said Letters Patent is hereby corrected as shown below:

On title page, item 73 Assignee,
replace "Bayer Cropscience LP, Monheim (DE)"
with --Bayer CropScience AG, Monheim (DE).--

Signed and Sealed this

Twenty-sixth Day of February, 2008

JON W. DUDAS
*Director of the United States Patent and Trademark Office*